(12) United States Patent
Fontanez

(10) Patent No.: US 7,930,772 B2
(45) Date of Patent: Apr. 26, 2011

(54) BLIND HEAD COOLING HELMET

(76) Inventor: Pedro Javier Fontanez, Mayaguez, PR (US)

( * ) Notice: Subject to any disclaimer, the term of this patent is extended or adjusted under 35 U.S.C. 154(b) by 739 days.

(21) Appl. No.: 11/927,556

(22) Filed: Oct. 29, 2007

(65) Prior Publication Data
US 2008/0184456 A1   Aug. 7, 2008

Related U.S. Application Data

(60) Provisional application No. 60/888,108, filed on Feb. 5, 2007.

(51) Int. Cl.
A63B 71/10 (2006.01)
(52) U.S. Cl. .......................................................... 2/425
(58) Field of Classification Search ................. 2/425
See application file for complete search history.

(56) References Cited

U.S. PATENT DOCUMENTS

| | | | |
|---|---|---|---|
| 2,049,723 A | 8/1936 | Pomeranz | |
| 2,158,571 A | 5/1939 | Culp | |
| 2,194,903 A * | 3/1940 | Holstein | 2/413 |
| 3,159,160 A | 12/1964 | Ullom et als. | |
| D225,088 S | 11/1972 | East | |
| 3,956,773 A | 5/1976 | Chisum | |
| 4,019,502 A | 4/1977 | Elkins | |
| 4,100,320 A * | 7/1978 | Chisum | 428/188 |
| 4,138,743 A | 2/1979 | Elkins et al. | |
| 4,147,921 A | 4/1979 | Walter et al. | |
| 4,250,577 A | 2/1981 | Smith | |
| 4,356,709 A | 11/1982 | Alexander | |
| D275,334 S | 9/1984 | Pullin | |
| 4,551,858 A * | 11/1985 | Pasternack | 2/7 |
| 4,552,149 A * | 11/1985 | Tatsuki | 607/110 |
| 4,586,200 A * | 5/1986 | Poon | 2/413 |
| 4,641,379 A | 2/1987 | Martin | |
| 4,653,124 A | 3/1987 | McNeal et al. | |
| 4,691,762 A | 9/1987 | Elkins et al. | |
| 4,753,242 A | 6/1988 | Saggers | |
| 4,765,338 A | 8/1988 | Turner et al. | |
| 4,781,193 A | 11/1988 | Padgen | |
| 4,783,866 A | 11/1988 | Simmons | |
| 4,893,356 A | 1/1990 | Waters | |
| 4,920,963 A | 5/1990 | Brader | |
| 4,921,141 A | 5/1990 | Branum | |
| 4,925,603 A | 5/1990 | Nambu | |
| 4,998,415 A | 3/1991 | Larsen | |
| 5,033,136 A | 7/1991 | Elkins | |
| 5,050,240 A | 9/1991 | Sayre | |
| 5,054,122 A | 10/1991 | Sher | |
| 5,054,475 A | 10/1991 | Calabrese et al. | |
| 5,119,812 A | 6/1992 | Angelo | |
| 5,190,032 A | 3/1993 | Zacoi | |
| 5,197,292 A | 3/1993 | McPherson | |
| 5,327,585 A | 7/1994 | Karlan | |
| 5,342,411 A | 8/1994 | Maxted et al. | |

(Continued)

*Primary Examiner* — Katherine Moran
(74) *Attorney, Agent, or Firm* — Carla Ferrari-Lugo; Roberto J. Rios

(57) ABSTRACT

Disclosed herein is a cooling device such as a blind head cooling helmet which will fully cover the head contour plus the area of the eyes, cheeks, and ears, having an lid arrangement with internal air ducts. An air pump generates and pushes small volumes of slow pace moving air, so that it be transferred to the blind head cooling helmet via an "C" shaped tube, to all the internal air duct, and finally escaping through the bottom of the lid arrangement, not without before the resulting air bubbles crashing against some areas of the internal layer creating a therapeutic effect or relaxing comfort to areas of the face.

15 Claims, 32 Drawing Sheets

U.S. PATENT DOCUMENTS

| | | |
|---|---|---|
| D354,376 S | 1/1995 | Kun |
| 5,395,400 A | 3/1995 | Staford et al. |
| 5,469,579 A | 11/1995 | Tremblay et al. |
| 5,474,533 A | 12/1995 | Ward et al. |
| 5,539,934 A | 7/1996 | Ponder |
| 5,542,413 A | 8/1996 | Horn |
| 5,557,807 A | 9/1996 | Hujar et al. |
| 5,603,728 A | 2/1997 | Pachys |
| 5,630,230 A | 5/1997 | Fujino et al. |
| 5,643,336 A | 7/1997 | Lopez'Claros et al. |
| 5,755,756 A | 5/1998 | Freedman, Jr. et al. |
| 5,897,581 A | 4/1999 | Fronda et al. |
| 5,950,234 A | 9/1999 | Leong et al. |
| 5,957,964 A | 9/1999 | Ceravolo |
| D420,493 S | 2/2000 | Blake |
| 6,050,099 A | 4/2000 | Lopa et al. |
| 6,554,787 B1 * | 4/2003 | Griffin et al. .................. 602/74 |

* cited by examiner

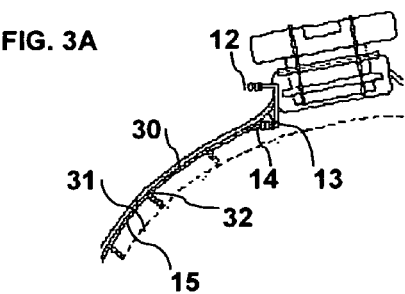
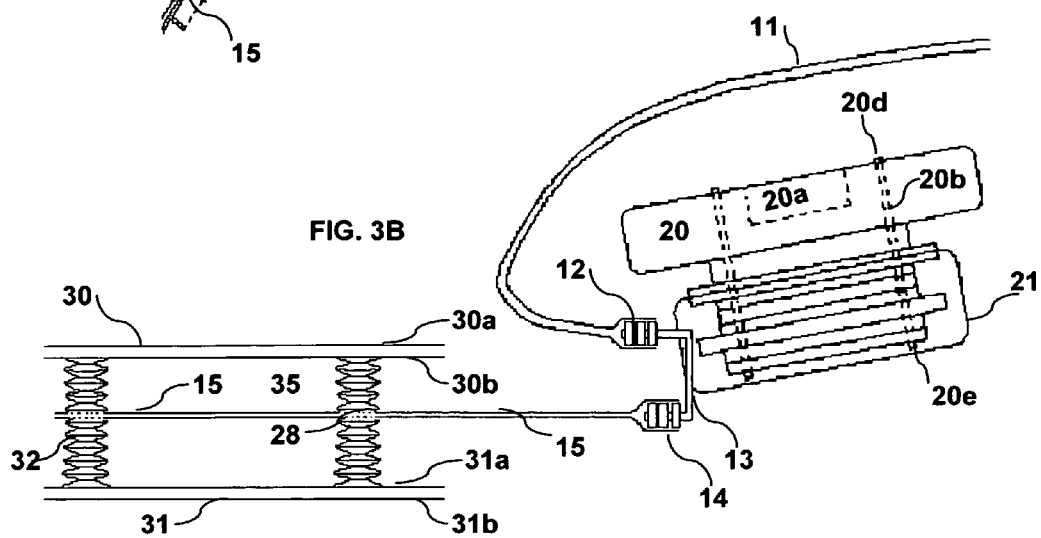
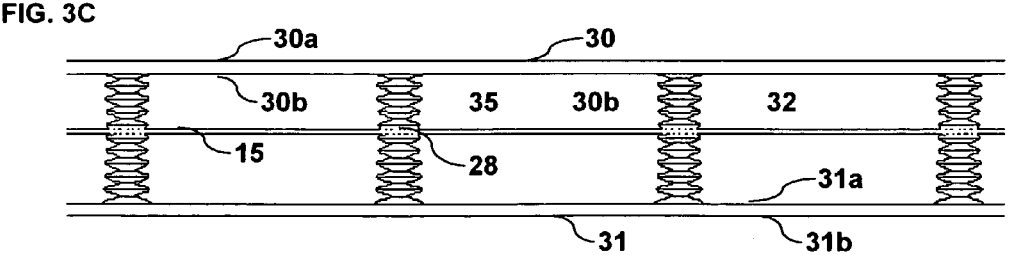
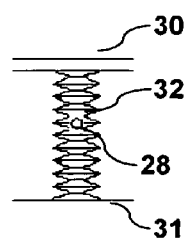

BLIND HEAD COOLING HELMET

CROSS REFERENCE TO RELATED APPLICATIONS

Not Applicable

FEDERALLY SPONSORED RESEARCH

Not Applicable

SEQUENCE LISTING OR PROGRAM

Not Applicable

FIELD OF THE INVENTION

The present invention relates to a head cooling device generally and in particular to a new full head contour cooling hat or head cooling helmet for controlling body temperature and relieving headache symptoms caused by various conditions such as migraines, sinusitis, head contusions or concussions or fever.

DESCRIPTION OF RELATED PRIOR ART

Due to the fact that the human head is very susceptible to the common headaches, migraine, sinusitis, head contusions, fever, and many other aches, it is sometimes necessary to decrease the abnormal temperatures and or discomforts produced by said aches. Artificial means such as the old water-ice bag, cold and hot therapies products, etc. have been used to alleviate these symptoms.

There have been prior attempts in the art in the form of similar cooling devices to decrease the abnormal temperatures and/or produce the cooling effect when applied on the human head, but none have been designed to cover other regions of the human head, such as the cheeks, ears and eyes. An example of said prior art we can find disclosed is in U.S. Pat. No. 5,957,964, issued Sep. 28, 1999 to Ceravolo. A cooling helmet is provided to cover the head contour, however, said invention does not cover the area of the eyes, cheeks and ears. U.S. Pat. No. 5,957,964 to Ceravolo also discloses the use of water to apply a cold effect as does the present invention, but it does not have the presence of permanent pockets filled with gel, or another semisolid-colloid materials, attached to its internal layer with empty cavities in association with permanent hollow water pockets attached to its parallel external layer with magnets, which provides both a cooling effect and pain relief therapy. Also, the present invention, unlike U.S. Pat. No. 5,957,964 to Ceravolo, discloses an air duct to carry small volumes of air to the interior of the blind head cooling helmet for the production of air bubbles, that will hit the layers, plus provide for the circulation of the water contained therein. Other patents describe some of the features used by Ceravolo, or other applications but none disclose the novel aspects of the present invention. The only patent that resembles the present invention is disclosed in U.S. D529,617, issued October 2006 to the present Inventor.

While the aforementioned prior art provide mechanisms to reduce body temperatures, none of them provide a device comprising a blind head cooling helmet or hat that covers all head contours to reduce body temperature and alleviate various aches while providing a therapeutic effect for the user.

Therefore, what is needed is a blind head cooling helmet that can cover all the contours of the head including the eyes, ears and cheeks to help resolve the need in the art. Problem. The implementation of small magnets adapting into small empty cavities, plus the circulation of the liquid medium by slow aeration produces a therapeutic effect in addition to a cooling effect to better serve this long felt need in the art.

SUMMARY OF THE INVENTION

The present invention solves the above references problems by providing a simple, efficient and practical device that helps reduce and/or decrease fever, aches, or discomforts produced by abnormal body temperatures and or headaches while also providing a therapeutic effect for the user. To achieve the foregoing and other advantages, the present invention, briefly described, provides a lightweight head cooling device such as a blind head cooling helmet that fits easily on the human head without the use of any elastic fastener or other means.

A preferred embodiment of the invention comprises a cooling device such as a blind head cooling helmet which comprises an external and internal layer joined in common edges resulting in the creation of a main hollow cavity that will be filled with water and/or other liquid medium to provide a cooling effect.

It is another aspect of the invention, to provide a cooling device such as a blind head cooling helmet with permanent hollow water pockets comprising at lease one small magnet permanently attached to its internal ceiling, both logistically located in the external layer to provide indirect contact to specific face muscles in order to specifically target discomfort and/or pain in said specific areas of the face.

Also, the present invention discloses a cooling device such as a blind head cooling helmet with pockets filled with gel and/or another colloid permanently attached to its internal layer with its respective empty cavities in order to further increase the cooling effect. The present invention also provides for the user to depress the water pockets comprising the magnet to allow the coupling or adaptation of the magnets with its respective water pockets from the external layer into the empty cavities of the gel pockets of the internal layer which helps alleviate pain and aches, while producing a therapeutic effect.

Another aspect of the present invention provides a cooling device such as a blind head cooling helmet that comprises an air pump for picking up small volumes of air and causing said small volumes of air to slowly move into a separate air line that will connect to the lid arrangement of the blind head cooling helmet to the interior cavity through a flexible air tube that will plug into the principal air line which will transport the small slow paced moving air from the air pump, sending it to an inverted "Y" shaped air tube to parallel perforated tubes finally joining in a common point or duct. The perforated tubes provide the slow paced moving air several points of escape through the perforated cavities in route to the top of the main hollow cavity or lid-lid base bottom, causing the air bubbles to crash against the areas that cover the eyes, cheeks, ears, etc, on the wet surface of the internal layer already comprising the liquid medium, which in a preferred embodiment comprises water, in order to produce a massage like sensation for alleviating discomfort and aches at the different areas of the face. In order for the bubbles to be released from said perforated tubes, another aspect of the invention comprises a lid arrangement with at least one internal small vertical tube for allowing the escape of the air produced from the resulting air bubbles.

In another embodiment of the present invention the cooling device comprises a lid arrangement with at least one small compartment for attaching, at least one watch, which in a preferred embodiment comprises a solar watch, to get track of the time when the blind head cooling helmet is placed inside the refrigerator, or for tracking the time said device has been worn by user.

Further, another aspect of the present invention comprises pins made up of at least one of flexible-elastic pins or shock absorbers, that will permanently support and separate the external layer of the blind head cooling helmet from the internal layer of said blind head cooling helmet, while at the same time providing an extended elasticity which produces a massage like effect when the water, or liquid medium circulates through its interior.

An advantage of the present invention is that the cooling device, such as a blind head cooling helmet comprises flexible and elastic materials which make it easy to wear and remove. Since it is designed to cover the eyes, cheeks and ears, it will not fall or slip away causing it to be securely adapted to the user's head.

A further advantage of the present invention is that the cooling device such as a blind head cooling helmet comprises a removable flexible thermometer, which in a preferred embodiment of the invention is located on of the forehead of the blind head cooling helmet, so that the user can track the temperature of the blind head cooling helmet inside any household appliance or simple cooling apparatus.

BRIEF DESCRIPTION OF THE DRAWINGS

The preferred embodiments of the invention will herein after be described in conjunction with the included drawings, which are provided only by way of illustration and not in limitation of the invention, and that various modifications may be made thereto without departing from the spirit of the invention as claimed, wherein like designations denote like elements, and in which;

FIG. 3A shows another cross-sectional view of the lid arrangement FIG. 2B but with the internal shock absorbers 32 being centrally penetrated 28 by the first submerged air tube 15 plus the external layer 30 and the internal layer 31.

FIG. 3B shows an enlarged view of the lid arrangement FIG. 2B and the description explained in FIG. 2B, FIG. 2G and FIG. 3A.

FIG. 3C shows another enlarged view of principal air duct 15 centrally fortified by the shock absorbers 32, plus the external layer 30 and its parallel internal layer 31 and the suggested presence of the liquid water 35 in between.

FIG. 3D shows a front view of the central hole 28 of the shock absorber 32 by where the principal air line 15 will pass through.

DETAILED DESCRIPTION OF THE PREFERRED EMBODIMENT

This specification and the accompanying figures disclose the preferred embodiment as example of the invention. The drawings illustrated in the figures are not to scale and are only intended to serve as illustrating examples of the invention. The invention is not intended to be limited to the embodiment illustrated. Numerous modifications, changes, variations, substitutions and equivalents will be apparent to those skilled in the art without departing from the spirit and scope of the present invention.

Figure 1A:
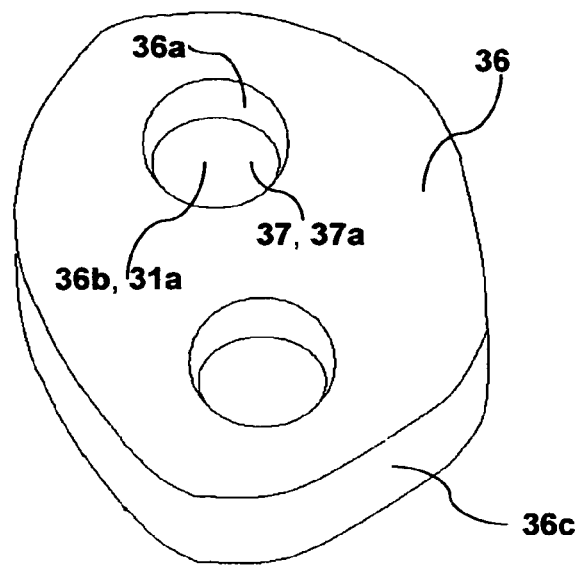
FIG. 1A shows a view of a gel pocket 36 with its respective empty cavity 37 where its internal walls 36a, floor 36b, 31a, and external walls 36c can be seen.
Figure 1B:
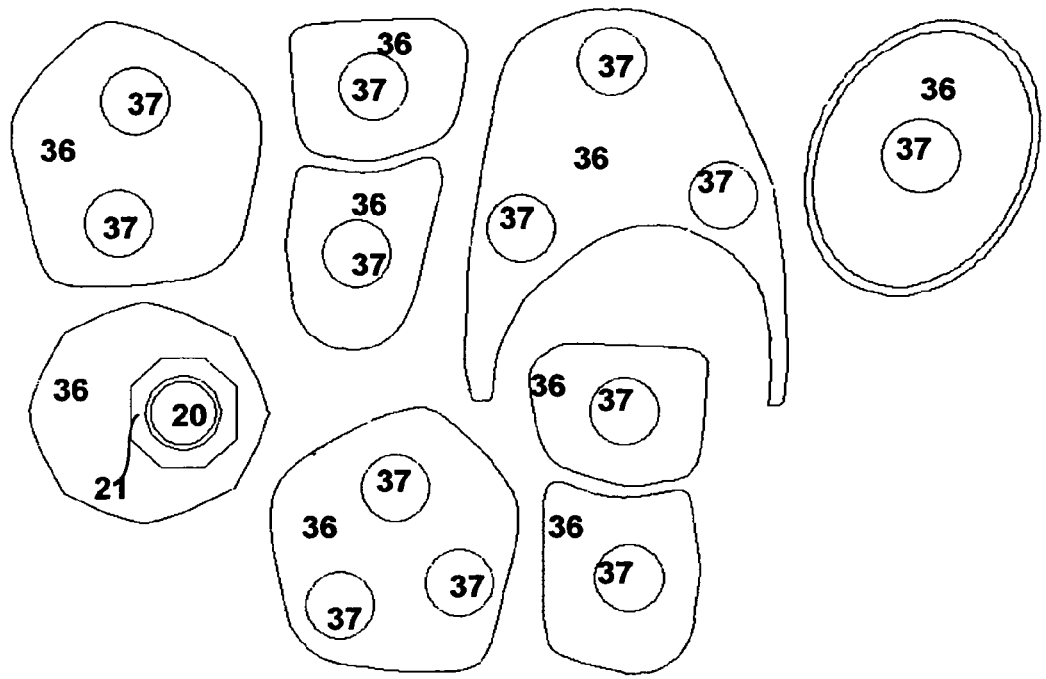
FIG. 1B shows a top view of the different forms and sizes of the gel pockets 36 with its respective hollow cavities 37.

Referring now to FIG. 1A and FIG. 1B the gel pockets 36 with its respective empty cavities 37, where the gel pockets are filled with enclosed gel or other colloid material, and its permanently attached to the internal layer 31, 31a not seen in this figure, of the blind head cooling helmet. Every pocket is made of flexible resistant elastic materials, such at least one of plastic, rubber, etc, so as to not produce any discomfort on the human head area were they are located. The gel pockets have an external wall 36c and at least one empty space or cavity 37 with internal walls 36a, internal floor 36b, 31a and top surface 37a. The gel pockets will be surrounded by liquid water and they will be selectively positioned around the entire contour of the blind head cooling helmet. The gel pockets have different sizes and shapes. Eventually every single empty space 37 will be adapted to its respective and parallel water pockets 38 and magnets 26, not seen in this drawing.

Figure 2A:
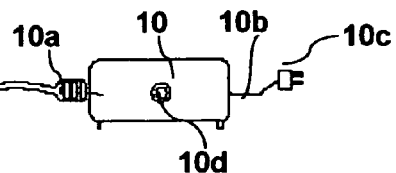
FIG. 2A shows a front view of an air pump 10 for picking up air from the exterior of the blind head cooling helmet and transferring it to the blind head cooling helmet via a long air line 11 for connecting it to the lid arrangement FIG. 2B and FIG. 2G, with its air-outlet 10a, its electrical cord 10b, its plug 10c and its air-inlet portion 10d.

Disclosed in FIG. 2A is an air pump with a body 10, an electrical cord 10b, a plug 10c, and an outlet 10d to pick up the air. Said pump 10 will generate small volumes of air and send it at slow pace into a separated flexible long air line 11, which as defined by inventor in this specification is referred to as intermediate skeleton, that will be plugged to the lid configuration FIG. 2B of the blind head cooling helmet, transferring the slow moved air into the exterior mouth 12 of the flexible air tub 13, which in a preferred embodiment comprises a "C" shaped air tube for allowing it to be transferred to its end portion 14 finally entering in another air duct 15, not seen in this drawing. FIG. 2C shows the top view of the lid 20 with one small square compartment 20a to temporally allocate a watch 25, which in a preferred embodiment comprises a solar powered digital watch, not seen in this drawing.

Figure 2B:
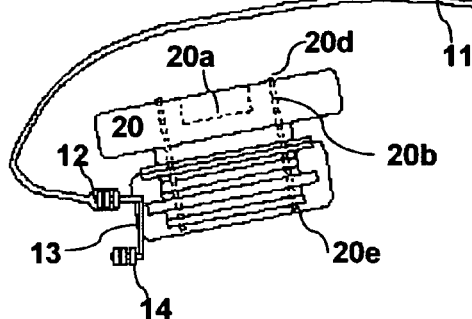
FIG. 2B shows a cross sectional view of the lid arrangement containing the lid 20, the small square compartment 20a for the small digital watch 25, not illustrated here, and the top mouth 20d of the vertical air tube 20b and its bottom mouth 20e, plus the long air line 11, the air-inlet 12 of the air tube, which in a preferred embodiment comprises a "C" shaped air tube, its body 13, and its air-out outlet 14 portion.
Figure 2C:
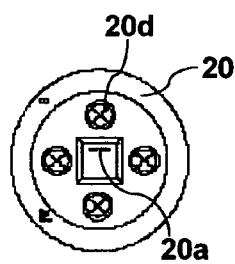
FIG. 2C shows a top view of the lid 20, the small square compartment 20a for the watch, not illustrated here, and the top portion 20d of the vertical tube 20b.
Figure 2D:
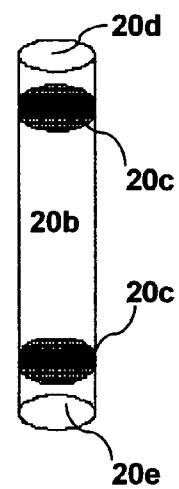
FIG. 2D shows a inclined view of the long vertical air tube 20b with its small round grates 20c in its interior, plus the top mouth 20d and its bottom end 20e portion.
Figure 2E:
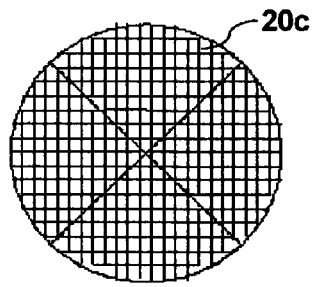
FIG. 2E shows a top view of the small multi perforated rounded grate 20c by where the released air will escape.
Figure 2F:
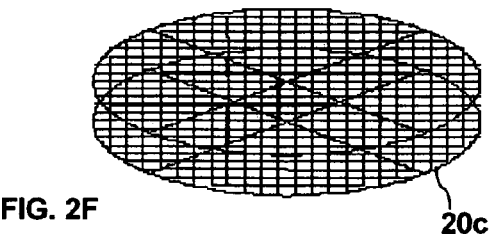
FIG. 2F shows an inclined view of the small rounded grate 20c of FIG. 2B, FIG. 2C, FIG. 2D and FIG. 2E.

The lid 20 has in its interior at least one small vertical hollow tube 20b, as seen in FIG. 2B and FIG. 2D with a top portion 20d, wherein the air from the interior of the blind head cooling helmet will escape to the exterior of the blind head cooling helmet through its bottom portion 20e, where the air from the interior of the blind head cooling helmet will enter, and finally at least one small rounded 20c net FIG. 2D, FIG. 2E and FIG. 2F, that will allow the air to escape but at the same time avoid the water to escape. The size of the vertical tubes can vary in width to facilitate the entrance and escape through its hollow interior.

Figure 2G:
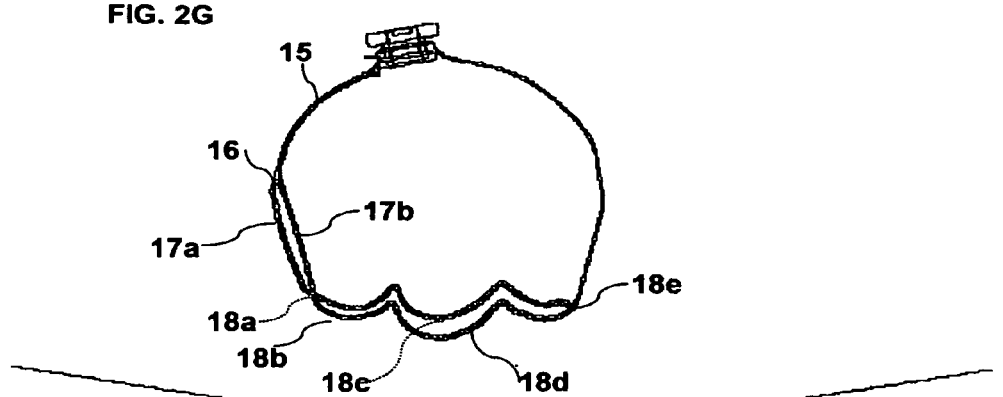
FIG. 2G shows a left side view of the blind head cooling helmet with the lid arrangement FIG. 2B with the rest of the air duct arrangement that includes the first submerged air tube 15 connecting to the inverted "Y" air tube 16, and the air tubes 17a, 17b, and perforated tubes 18a, 18b, 18c, 18d and 18e.
Figure 2H:
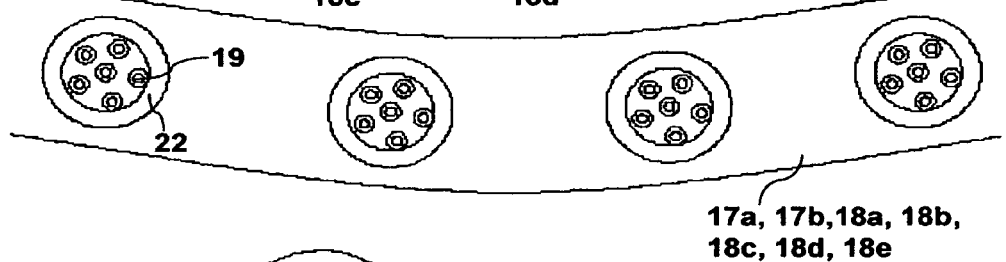
FIG. 2H and FIG. 2I shows a enlarged view of the air tubes 17a, 17b, and perforated tubes 18a, 18b, 18c, 18d and 18e with its respective holes 19 and its body 22.
Figure 2I:
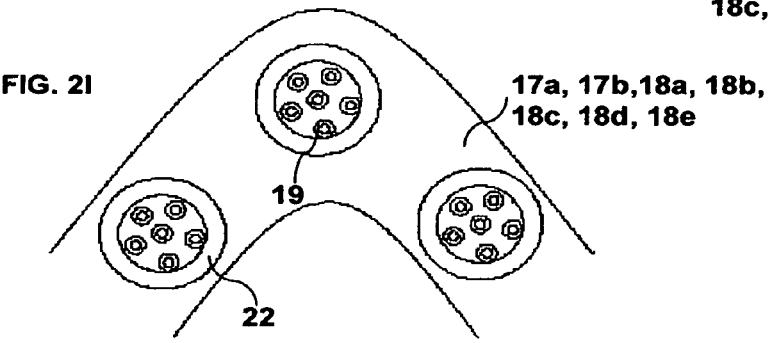

FIG. 2G shows the blind head cooling helmet with the entire air duct arrangement, also referred to by the inventor as the intermediate skeleton, that includes the first submerged air tube 15 connecting to the inverted "Y" air tube 16, and the air tubes 17a, 17b, and the perforated air tubes 18a, 18b, 18c, 18d and 18e which will cause the slow pace moving air to escape in the form of air bubbles as shown in FIG. 2H and FIG. 2I.

Figure 6:
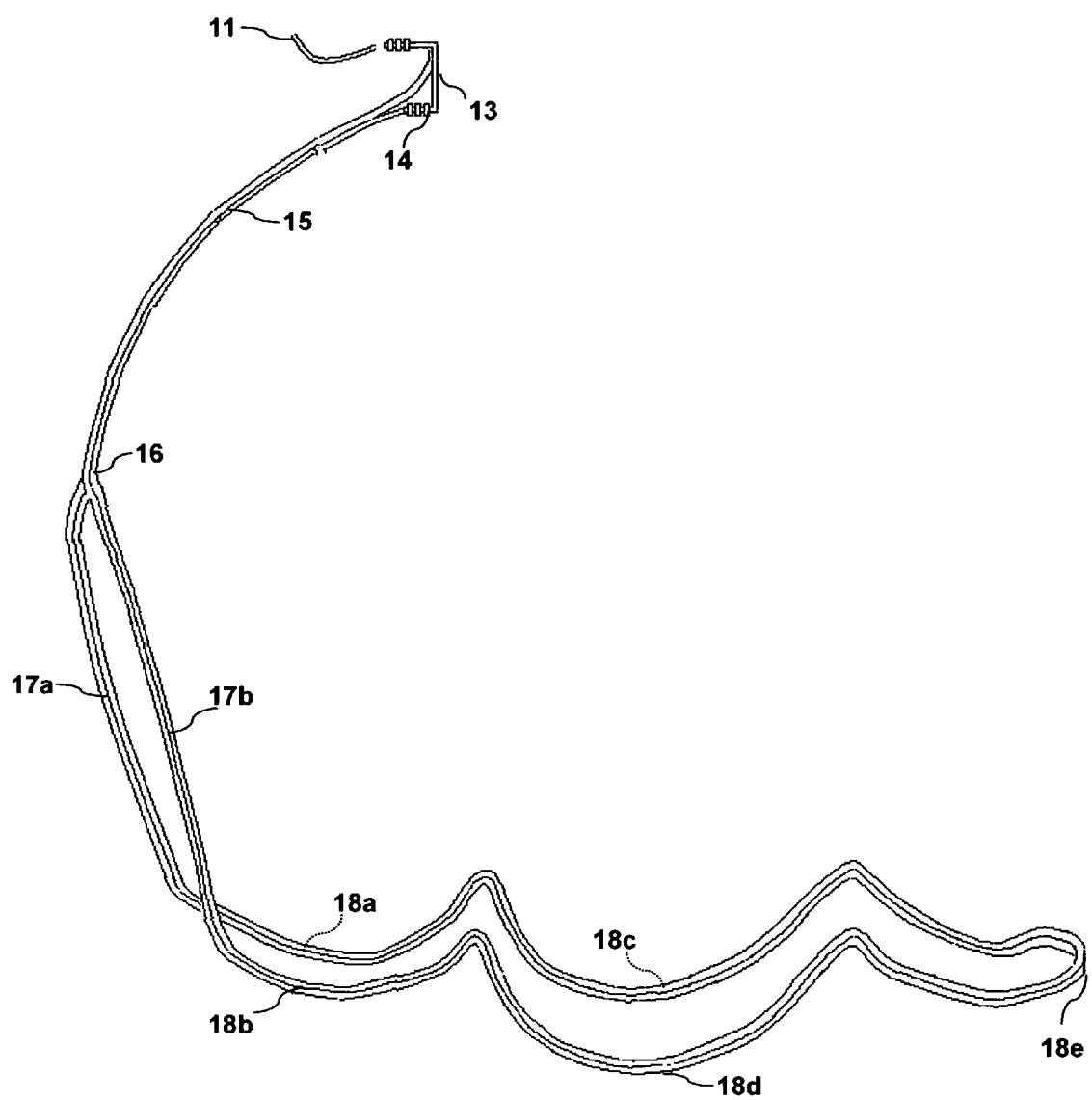
FIG. 6 shows a left side view of the air ducts described in FIG. 2G, FIG. 2H and FIG. 2I.

FIG. 6 shows a left side view of the entire air duct arrangement or intermediate skeleton.

Figure 13:
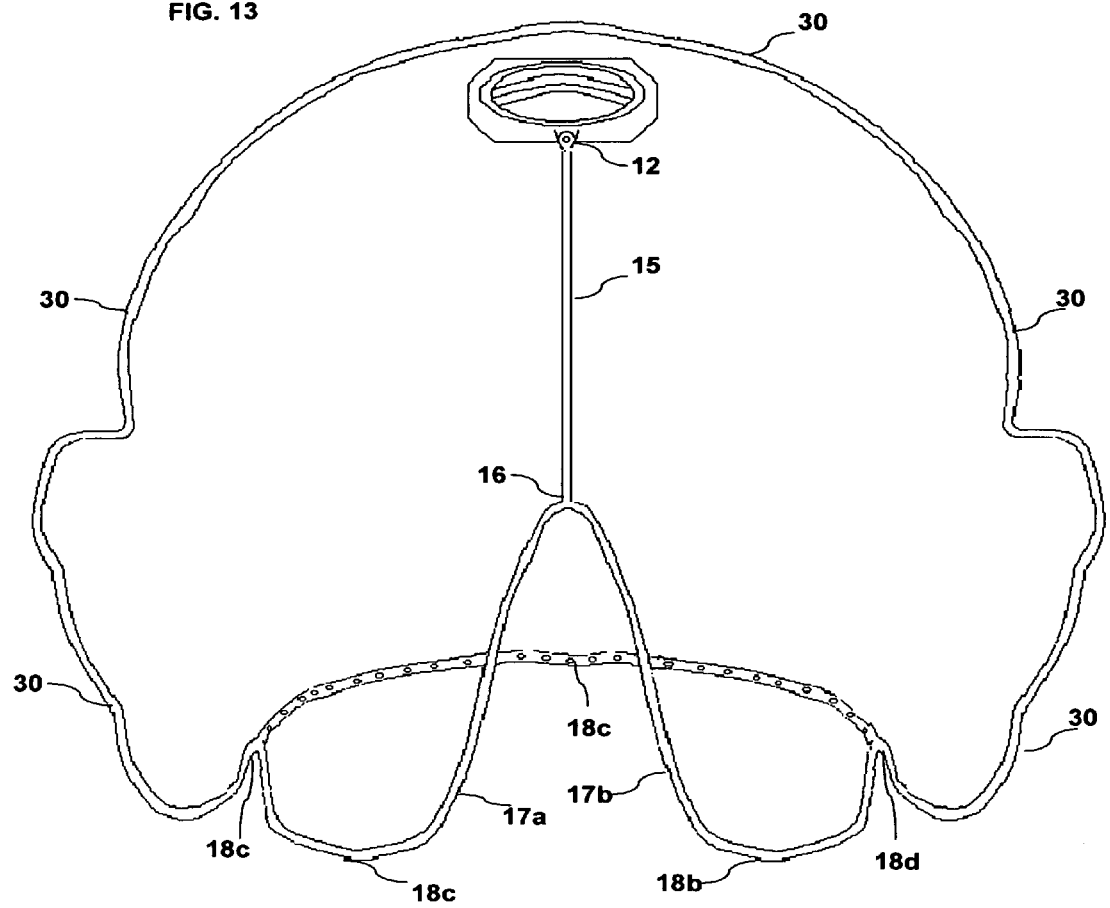
FIG. 13 shows a front view of the air duct arrangement (or intermediate skeleton), seen in FIG. 2G, FIG. 3A, FIG. 3B and FIG. 6, and the perforated air ducts seen in FIG. 2H and FIG. 2I.
Figure 14:
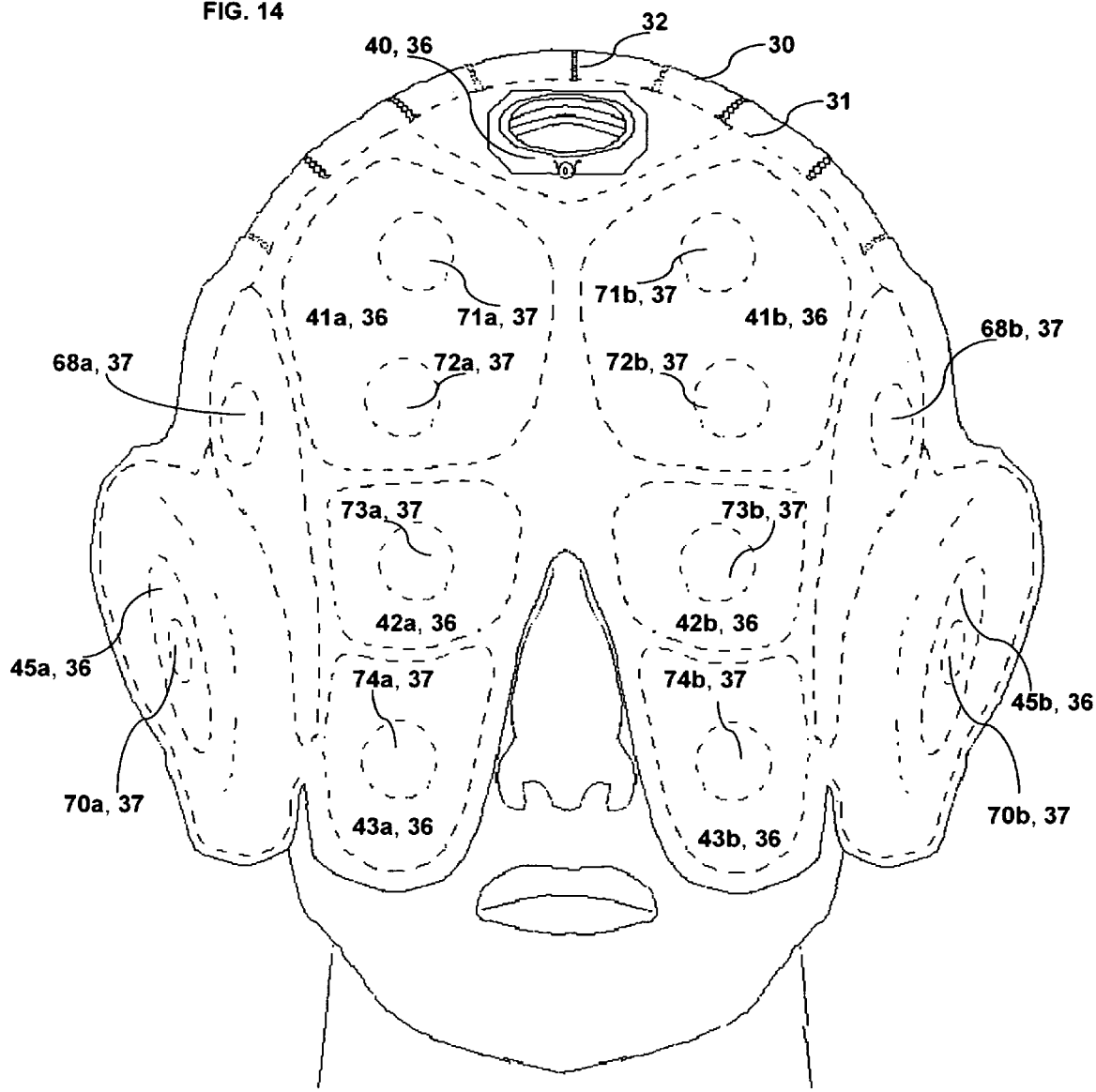
FIG. 14 shows another front side view of the blind head cooling helmet, with the internal layer 31 in dashed lines, as seen in FIG. 7, with the gel pockets 36 and its respective empty cavities 37, where each one will be fully described in the Detailed Description of the Preferred Embodiment.
Figure 15:
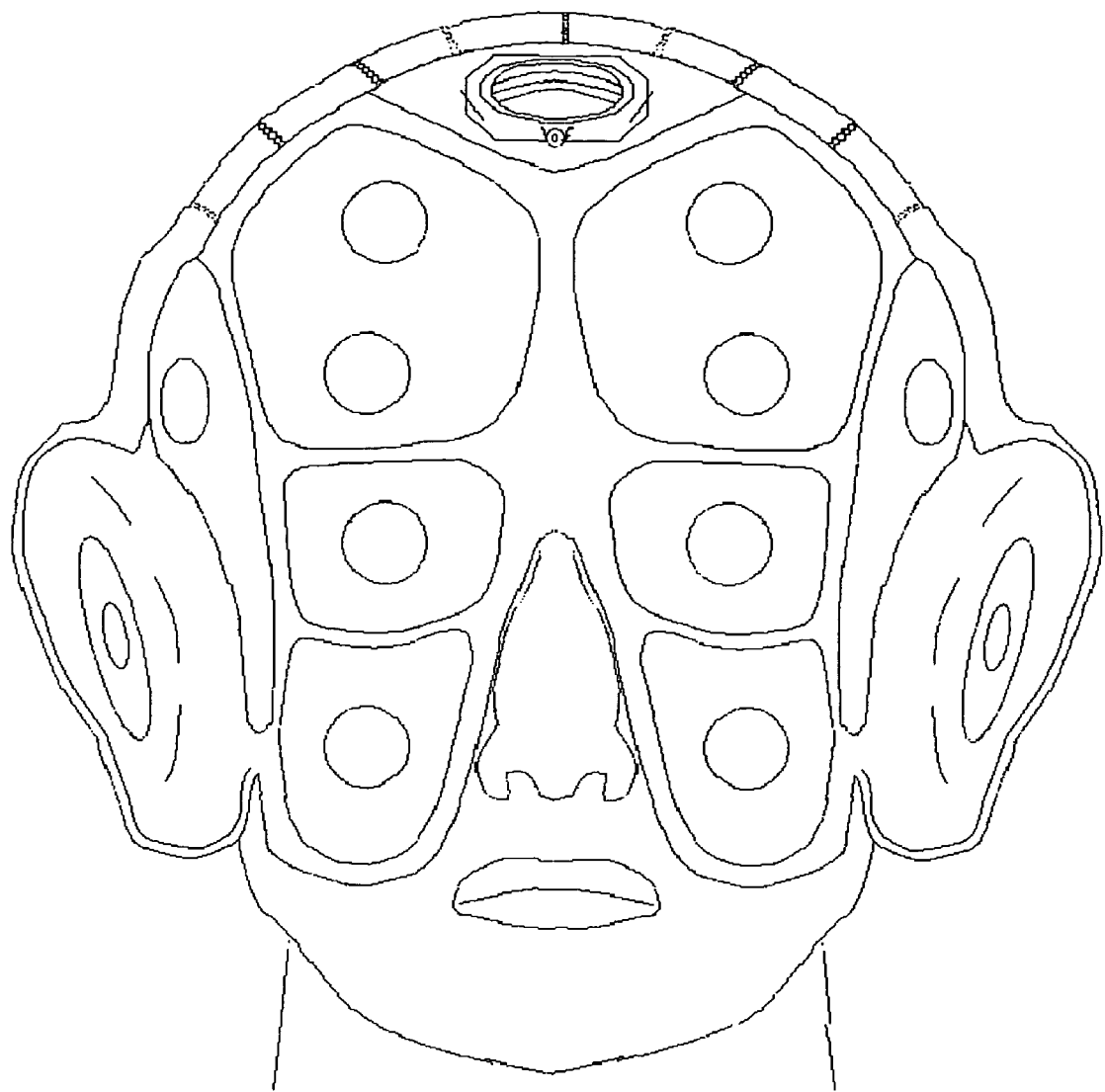
FIG. 15 shows the same FIG. 14 but the lines are solid.

FIG. 13 is a front side view of the entire air duct arrangement or the intermediate skeleton.

FIG. 3A, FIG. 3B, FIG. 3C and FIG. 3D show the pins or shock absorbers 32, which in a preferred embodiment comprise a material such as at least one of flexible elastic material that will be attached to the external layer 30 and the internal layer 31, keeping them together and creating a main hollow cavity in between where the liquid water 35 or another liquid medium will be enclosed to produce the cooling effect. The shock absorbers will be selectively positioned or located around the entire contour of the blind head cooling helmet but will not be covering the central surfaces or roofs of the gel pockets 38, not seen in this drawing, except some areas of the top central gel pocket 40, also not seen in this drawing. Only the shock absorbers that are located from the forehead area to the inverted "Y" air tube are centrally hollow FIG. 3D to contain the passage of the first submerged air tube 15 connecting to the inverted "Y" air tube 16, but the remaining shock absorbers are solid and made up of at least one of a flexible or elastic material.

The external layer 30 has an external dry surface 30*a* in contact with the air and its internal surface 30*b* will be wet when in contact with water 35; its parallel internal layer 31 has an external surface 31*a* which is wet when in contact with the water but its internal dry surface 31*b* will be dry and in direct contact with the human head's skin when the blind head cooling helmet is on.

Figure 4A:
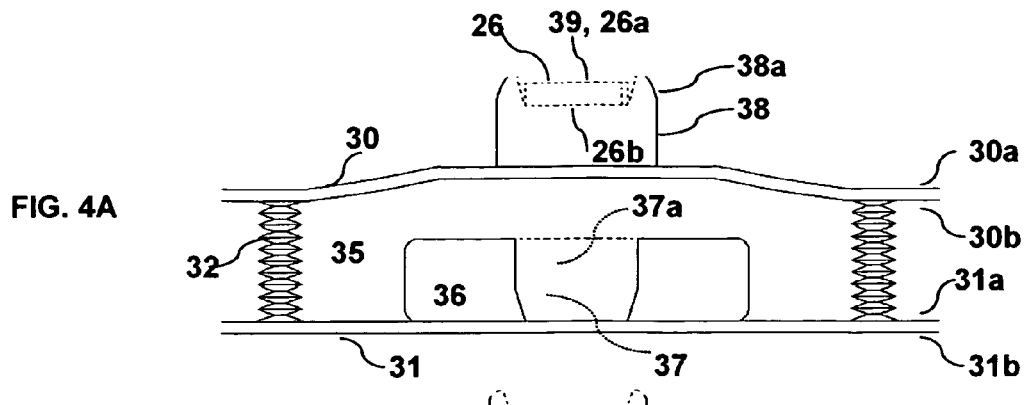
FIG. 4A shows an enlarged cross section view of the first taken (normal) position of one hollow water pocket 38 with its hanging magnet 26 facing down its respective parallel empty cavity 37 of the pertaining gel pocket 36, plus the shock absorbers 32 separating the respective external layer 30 and the internal layer 31.
Figure 4B:
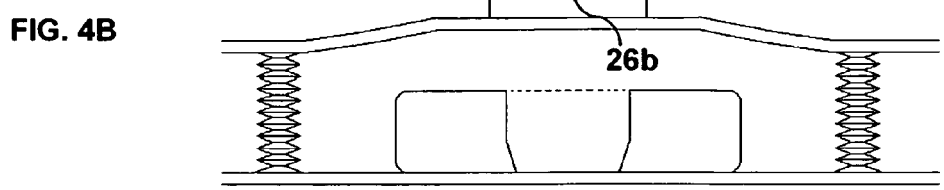
FIGS. 4B-4G show cross section views of the water pockets 38 as being depressed or actuated by user in order to cause the magnet 26 to adapt to the parallel empty cavity 37 of the gel pockets 36.
Figure 4C:
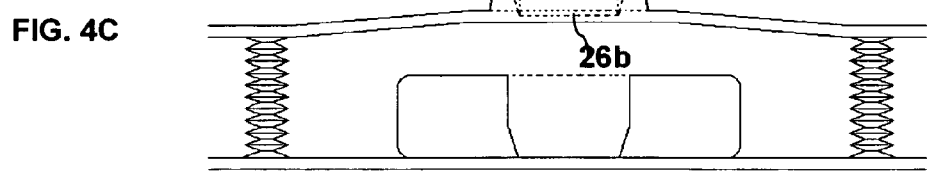
Figure 4D:
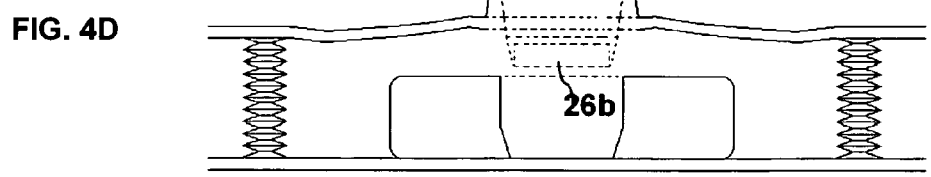
Figure 4E:
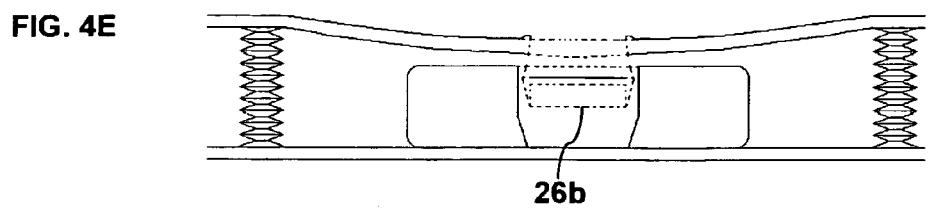
Figure 4F:
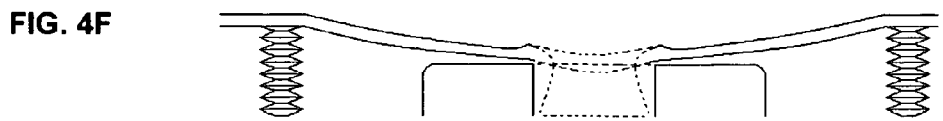
Figure 4G:
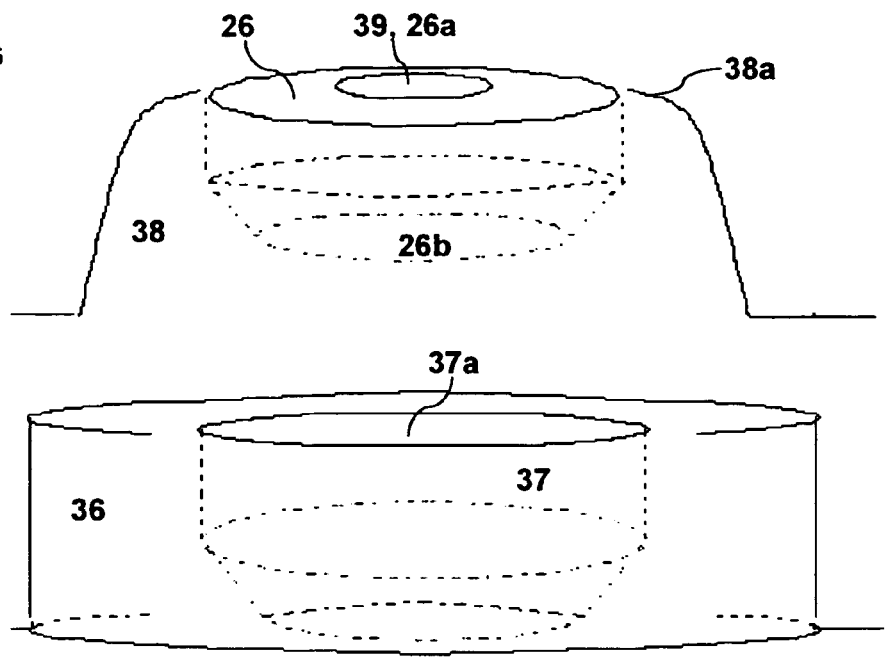
Figure 4H:
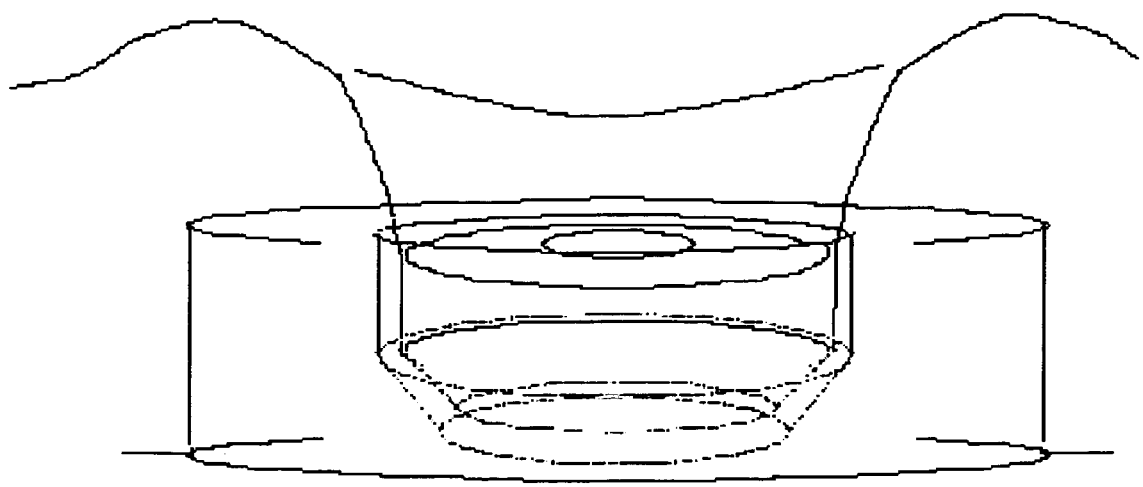
FIG. 4H shows an enlarged cross section view of the water pocket-magnet arrangement coupling inside its parallel gel pockets arrangement.
Figure 5:
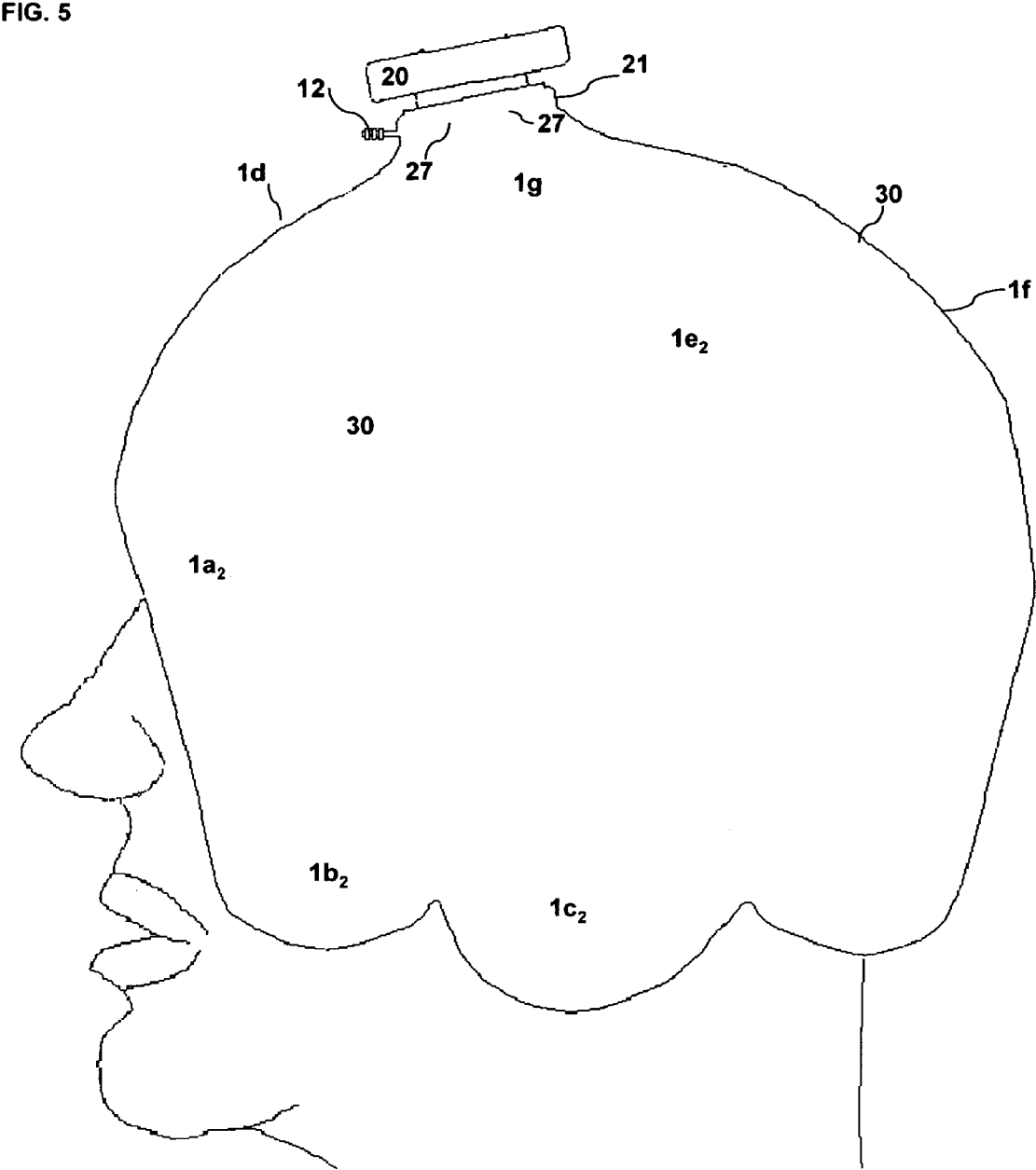
FIG. 5 shows a left side view of the blind head cooling helmet with its lid arrangement FIG. 2B at the top 1g, a dome-like harder plastic 27, and covered forehead 1d, left side $1e_2$, left ear $1c_2$, left eye $1a_2$, left cheek $1b_2$ and back 1f.

FIG. 4A to FIG. 4F shows the elasticity of the water pocket 38 when user presses down the roof 39 of the water pocket into its respective parallel empty cavity of its gel pocket 36 and coupling configuration. When the water pocket is slowly actuated its near external layer 30 also will be pulled down with it at the same time. FIG. 4A shows the normal shape and form of the water pocket when it is not actuated by user. When user releases the water pocket it reverts automatically to its original form and shape FIG. 4A. It is called water pocket because this hollow dome-like feature is in direct contact with the water from the main hollow cavity. The idea of this process is to proportionate a soft pressure or massage-like effect with the small magnet 26 attached in the ceiling of the water pocket over the floor 36*b* (the same external surface 31*a* of the internal layer 31) of the empty cavity. It is believed that magnets are capable of producing therapeutic effects in humans. Plus, FIG. 4G and FIG. 4H are enlarged cross section views of FIG. 4A and FIG. 4F.

FIG. 5, FIG. 12, FIG. 19 and FIG. 25 show the blind head cooling helmet, where the lid 20 is attached to the lid, by any attachable means such as at least one of screws, Velcro, etc., down into its lid base 21, that is built onto a dome-like harder elastic plastic 27, so the lid will not make contact with the top of the internal layer touching the human head. The blind head cooling helmet comprises a forehead 1*d* section, a back 1*f*, a right side 1*e*₁, a left side 1*e*₂, the covered right eye 1*a*₁ and left eye 1*a*₂, the covered right ear 1*c*₁ and left ear 1*c*₂, and the covered right cheek 1*b*₁ and left cheek 1*b*₂.

A thermometer 75 is located on the forehead 1*d* section of the blind head cooling helmet, which in a preferred embodiment comprises a small flexible and comfortable digital thermometer. Said thermometer is removable and attached to the blind head cooling helmet. In a preferred embodiment of the invention the thermometer uses liquid crystal technology to indicate the temperature of the blind head cooling helmet when it is storage inside the refrigerator to allow the water to cool. It may use a dyed red alcohol instead of the toxic mercury.

Figure 7:
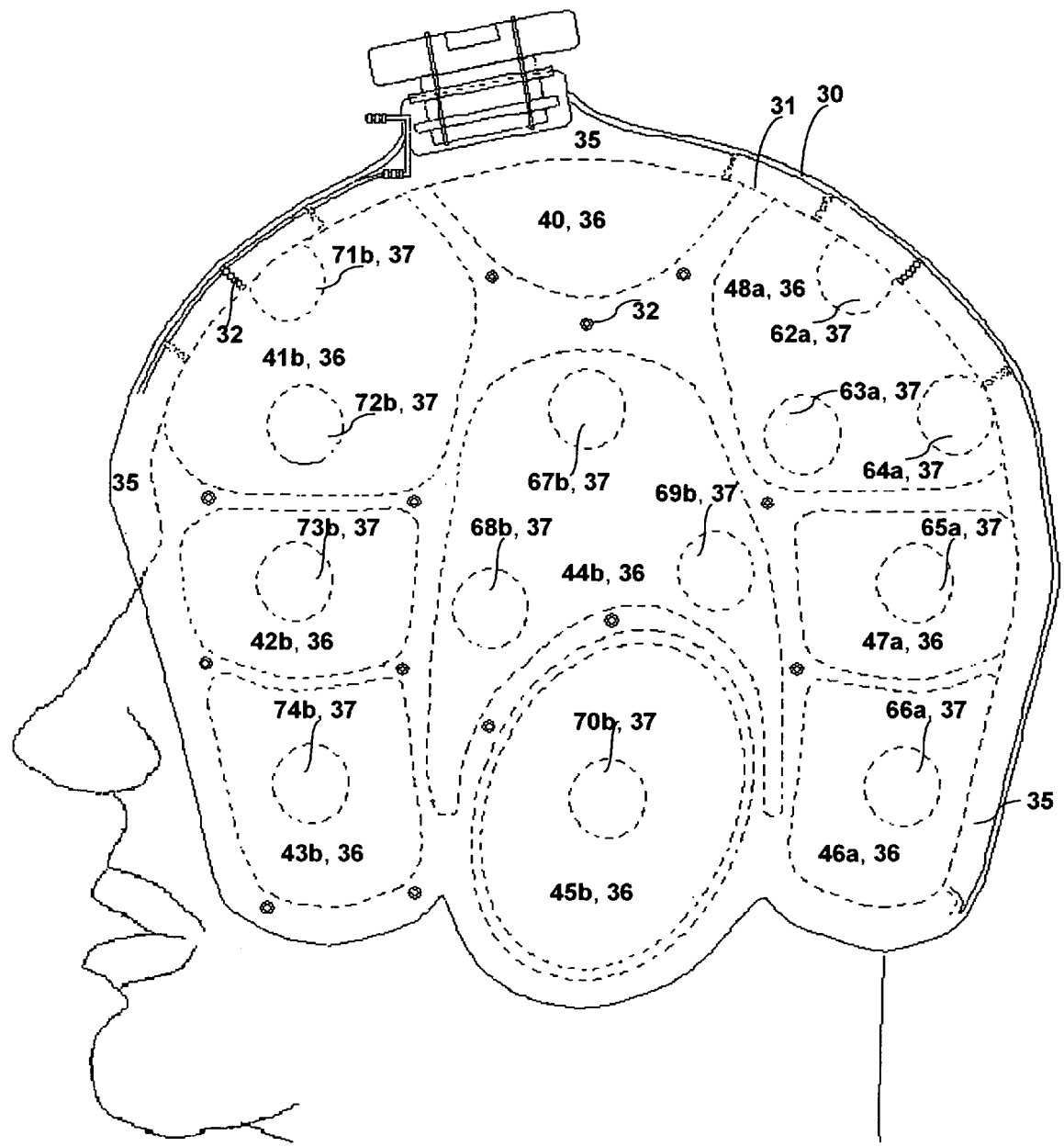
FIG. 7 shows a left side view of the blind head cooling helmet, with the internal layer 31 in dashed lines, with the gel pockets 36 and its respective empty cavities 37.
Figure 8:
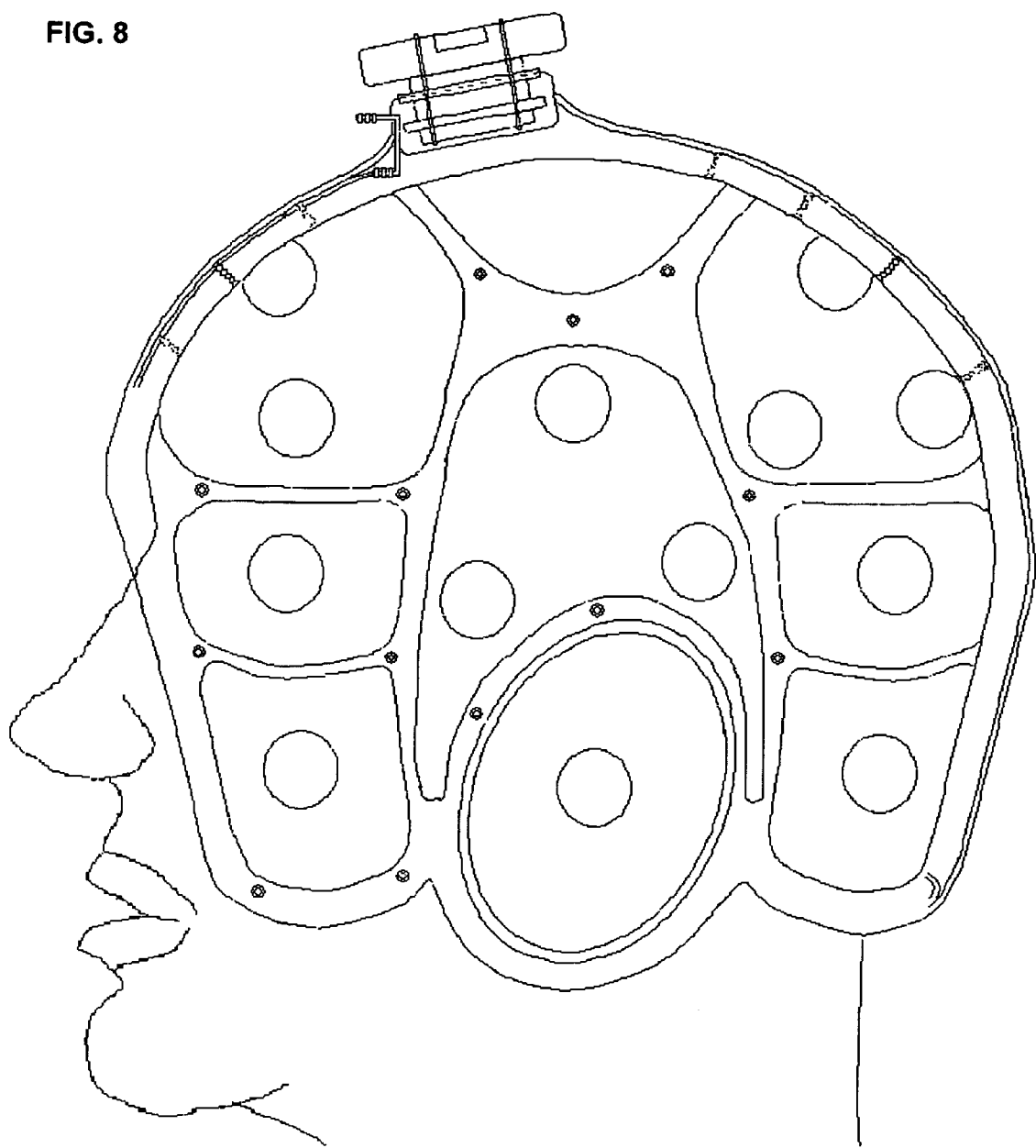
FIG. 8 shows FIG. 7 in solid lines.

FIG. 7, FIG. 14, FIG. 20 and FIG. 26 show the internal layer 31, in dashed lines, of the blind head cooling helmet with the gel pockets 36 with its respective empty cavities 37 together. In a preferred embodiment, the left side of FIG. 7 shows the right forehead gel pocket 41*b* with its respective empty spaces 71*b*, 72*b*; the left ocular gel pocket 42*b* have only one empty cavity 73*b*, the left cheek gel pocket 43*b* have one cavity 74*b*, the left mid side gel pocket 44*b* have three empty spaces 67*b*, 68*b* and 69*b*; the left ear gel pocket 45*b* have only one cavity 70*b*; the left-back bottom gel pocket 46*a* have its empty cavity 66*a*; the left mid back gel pocket 47*a* have its empty space 65*a*, the left upper back gel pocket 48*a* have also three cavities 62*a*, 63*a* and 64*a*, but the top central gel pocket 40 have not any empty space. FIG. 7 shows the shock absorbers 32.

FIG. 9, FIG. 16, FIG. 22 and FIG. 28 show the internal layer 31, in dashed lines, of the blind head cooling helmet with the water pocket-magnet arrangement 38, 26 overlapping its respective parallel gel pocket-empty cavity arrangement 36,37 at the same time. In a preferred embodiment, in FIG. 9, the left side view of the blind head cooling helmet, water pocket-magnet arrangement 58*b* will adapt into its parallel gel pocket-empty cavity arrangement 71*b*, 41*b*; water pocket-magnet arrangement 59*b* will adapt into its parallel gel pocket-empty cavity arrangement 72*b*, 41*b*; water pocket-magnet arrangement 60*b* will adapt into its parallel gel pocket-empty cavity arrangement 73*b*, 42*b*; water pocket-magnet arrangement 61*b* will adapt into its parallel gel pocket-empty cavity arrangement 74*b*, 43*b*; water pocket-magnet arrangement 54*b* will adapt into its parallel gel pocket-empty cavity arrangement 67*b*, 44*b*; water pocket-magnet arrangement 55*b* will adapt into its parallel gel pocket-empty cavity arrangement 68*b*, 44*b*; water pocket-magnet arrangement 56*b* will adapt into its parallel gel pocket-empty cavity arrangement 69*b*, 44*b*; water pocket-magnet arrangement 53*a* will adapt into its parallel gel pocket-empty cavity arrangement 66*a*, 46*a*; water pocket-magnet arrangement 52*a* will adapt into its parallel gel pocket-empty cavity arrangement 65*a*, 47*a*; water pocket-magnet arrangement 49*a* will adapt into its parallel gel pocket-empty cavity arrangement 62*a*, 48*a*; water pocket-magnet arrangement 50*a* will adapt into its parallel gel pocket-empty cavity arrangement 63*a*, 48*a*; and finally the water pocket-magnet arrangement 51*a* will adapt into its parallel gel pocket-empty cavity arrangement 64*a*, 48*a*.

Figure 16:
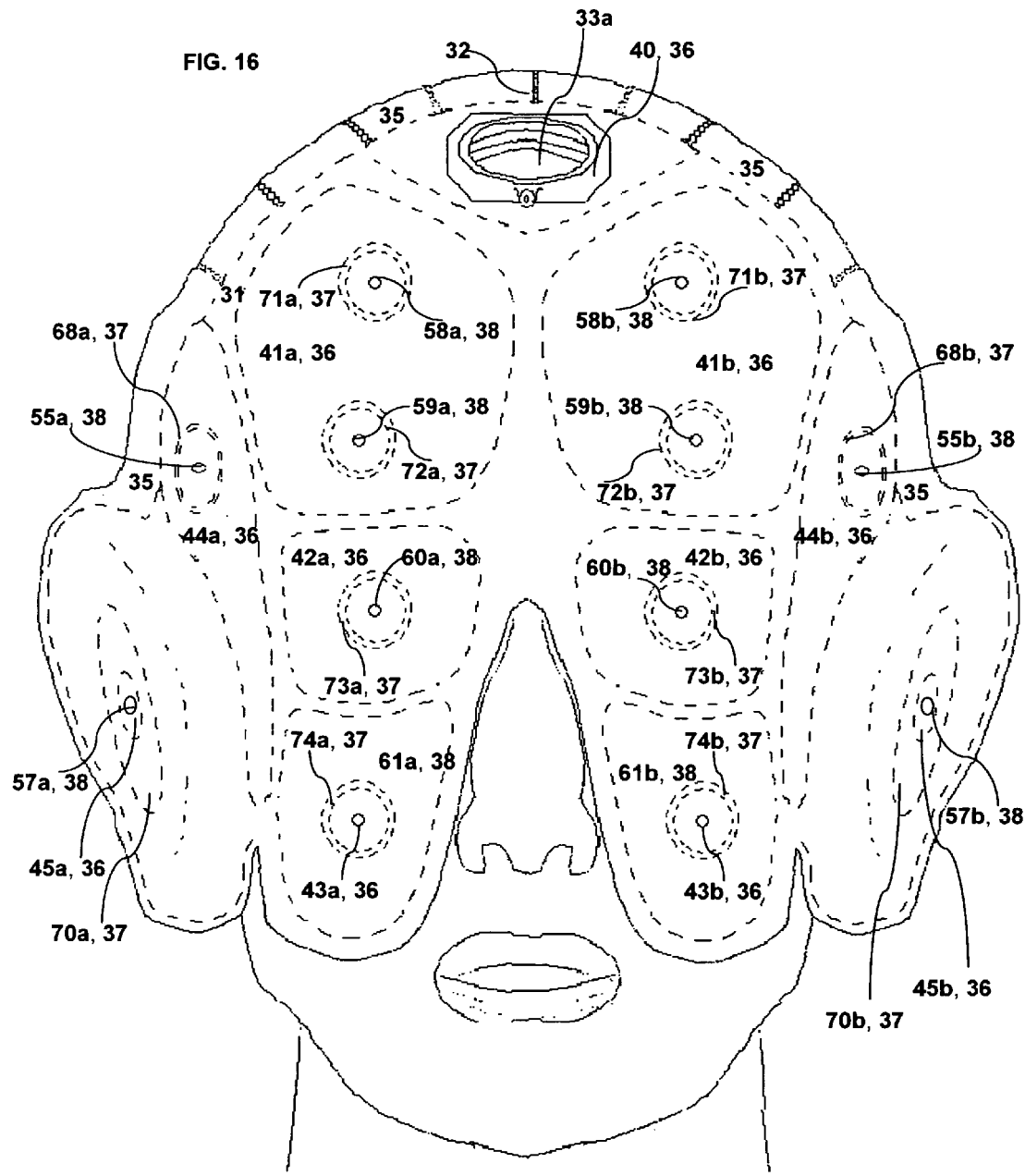
FIG. 16 shows the front side view of the blind head cooling helmet, with the internal layer 31 in dashed lines, as seen in FIG. 9, with the empty cavities 37 of its respective gel pockets 36 being overlapped or adapted in with its respective parallel water pockets 38 and magnets 26.
Figure 17:
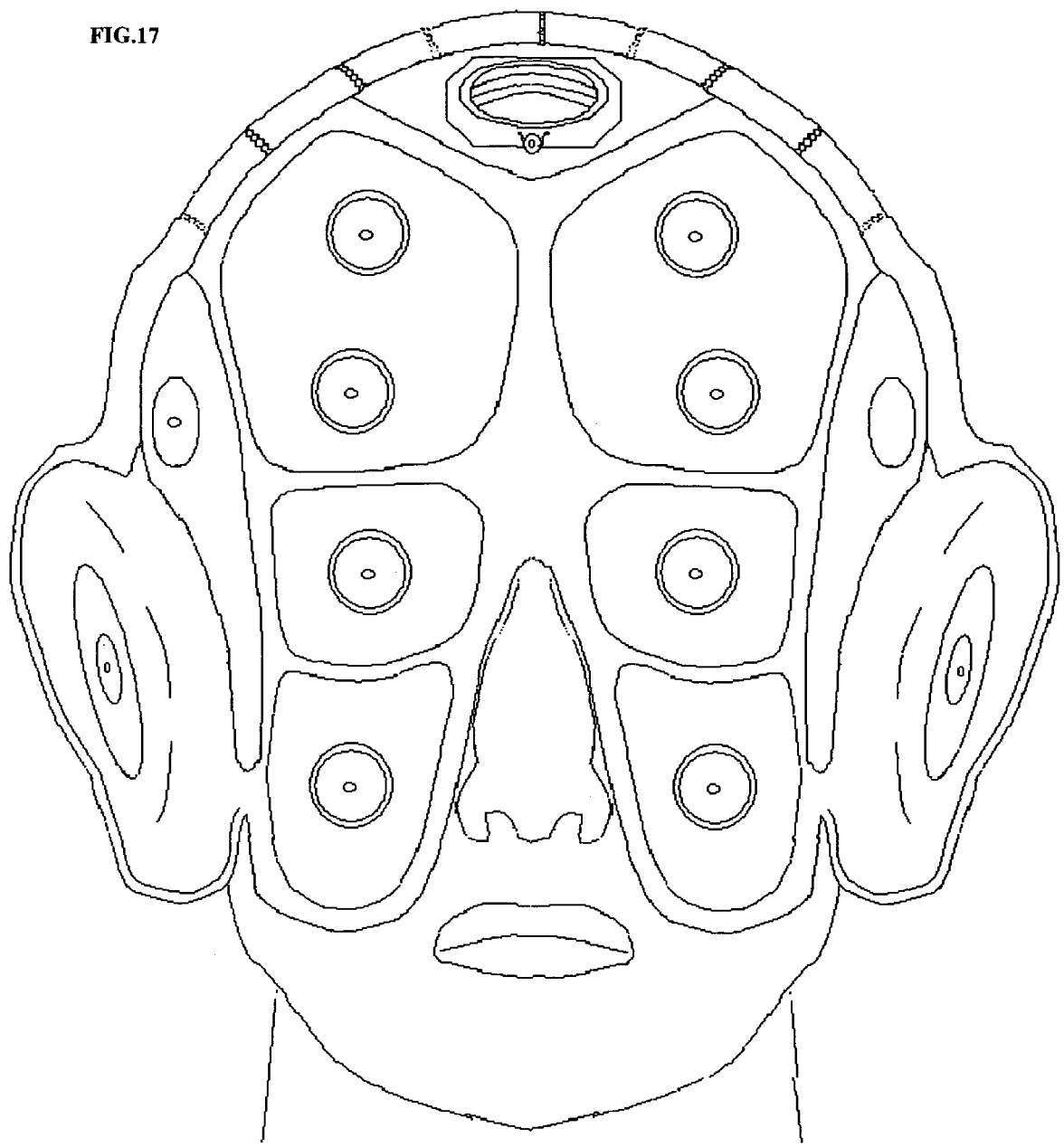
FIG. 17 shows FIG. 16 in solid lines.
Figure 18:
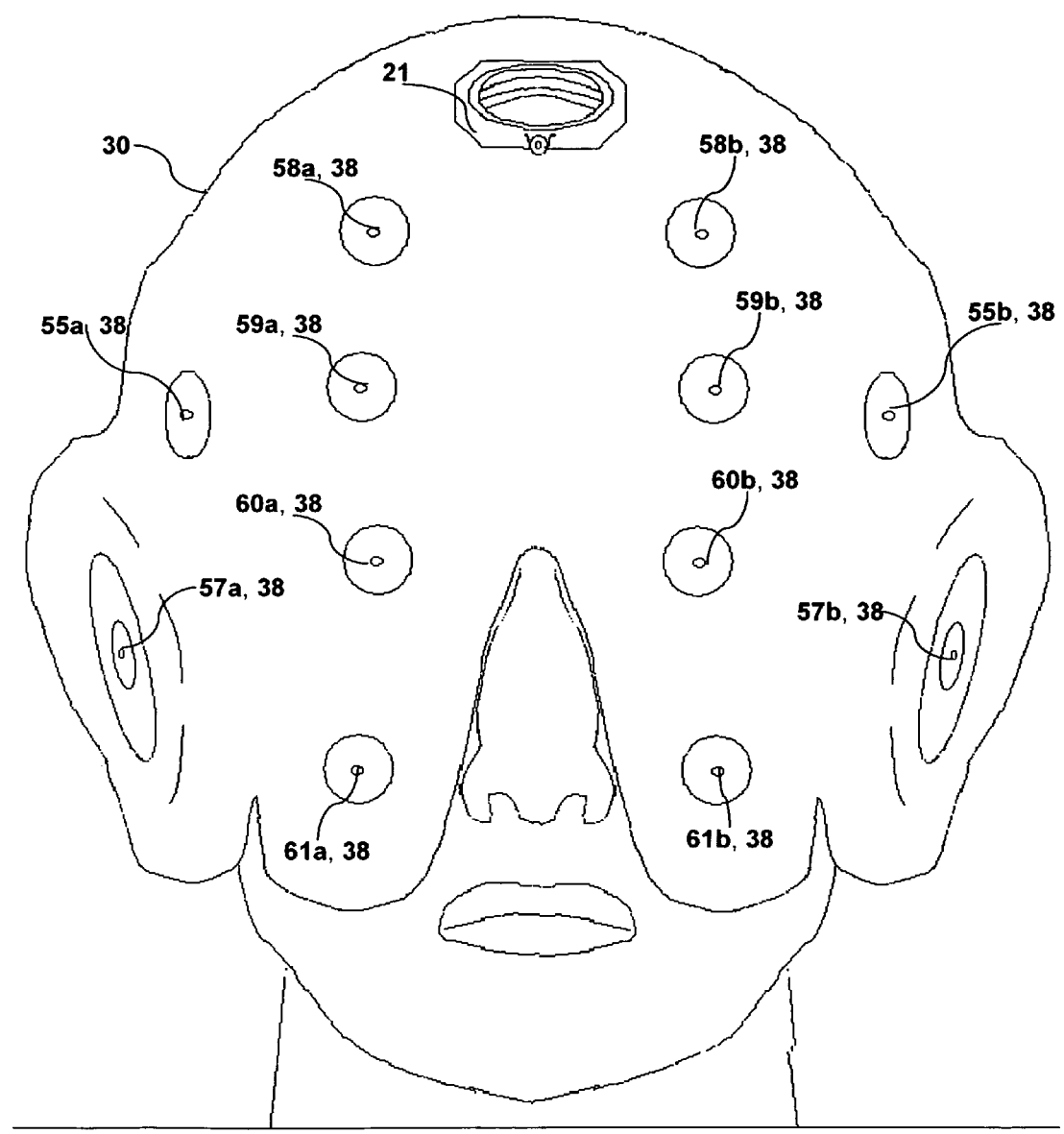
FIG. 18 shows a front view of the blind head cooling helmet with its external surface 30, as described in FIG. 11, with the external dry surfaces of the water pockets 38 and its respective tops or peaks 39 (dry roof 26a of the magnet 26).
Figure 19:
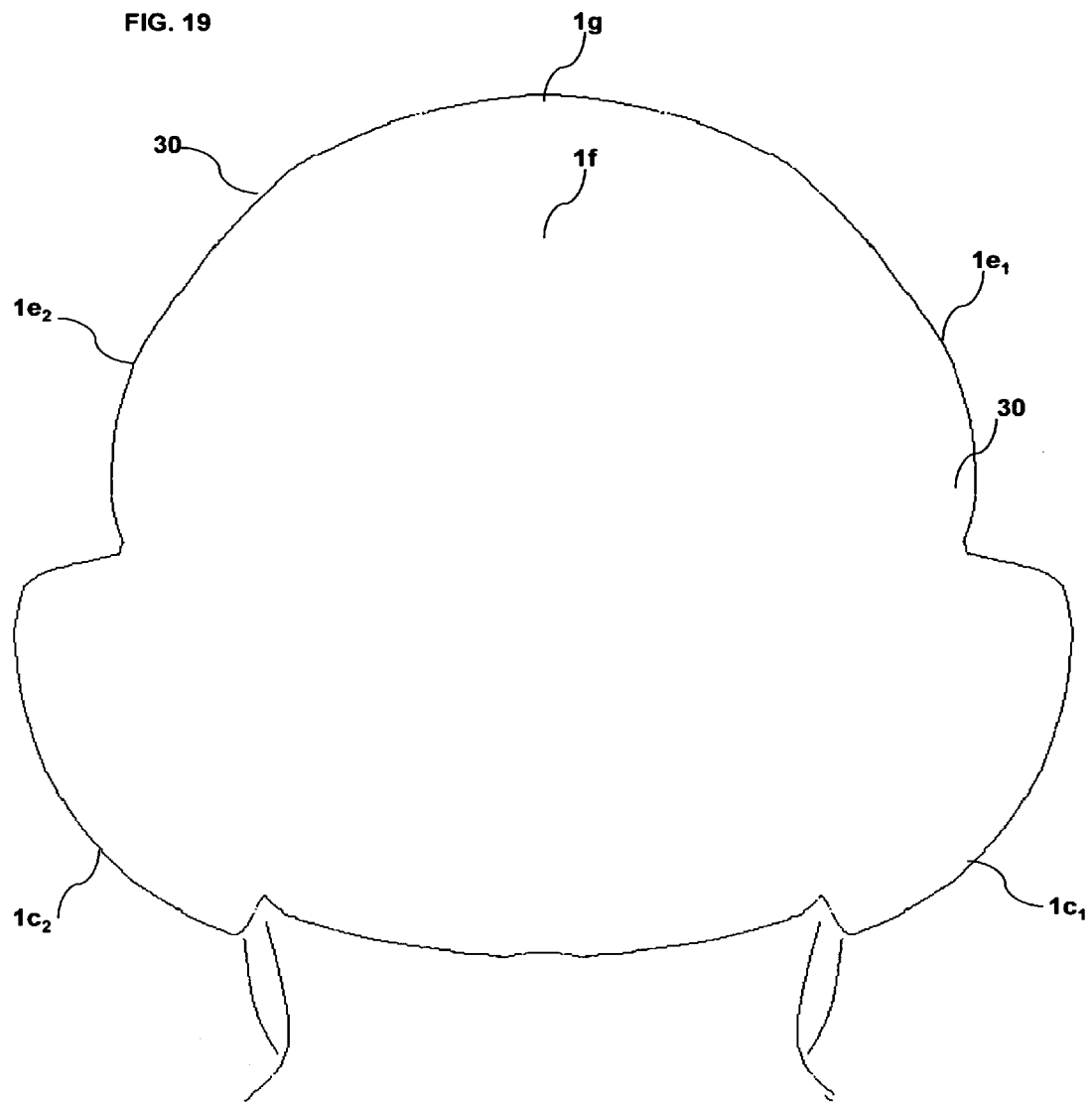
FIG. 19 shows the back side view of the blind head cooling helmet described in FIG. 5 and FIG. 12 with the top 1g, fore back 1f and covered left side $1e_2$, right side $1e_1$, left ear $1c_2$ and right ear $1c_1$.
Figure 20:
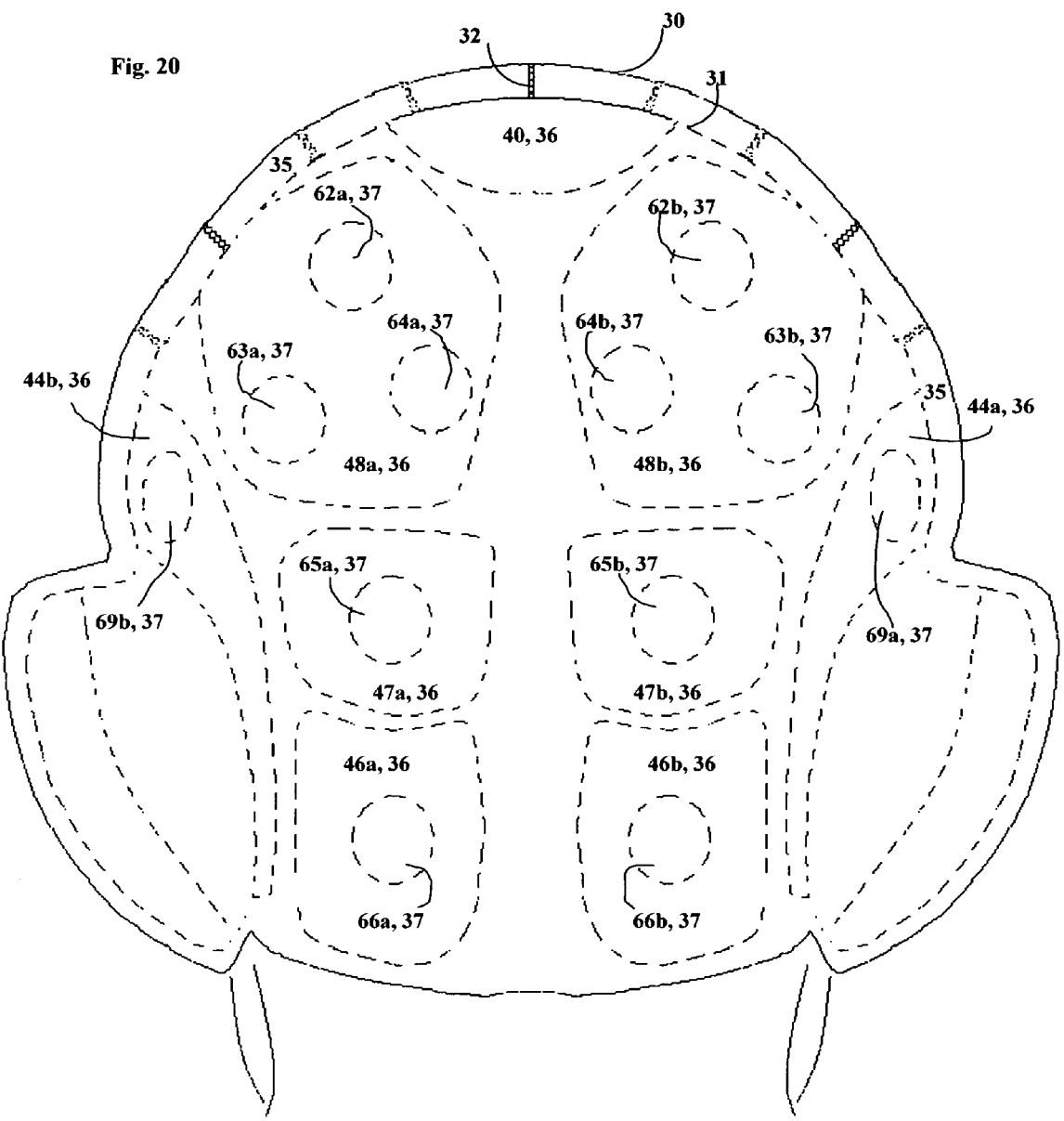
FIG. 20 shows the back side view of the blind head cooling helmet, with the internal layer 31 in dashed lines, as seen in FIG. 7 and FIG. 14, with the gel pockets 36 and its respective empty cavities 37.
Figure 21:
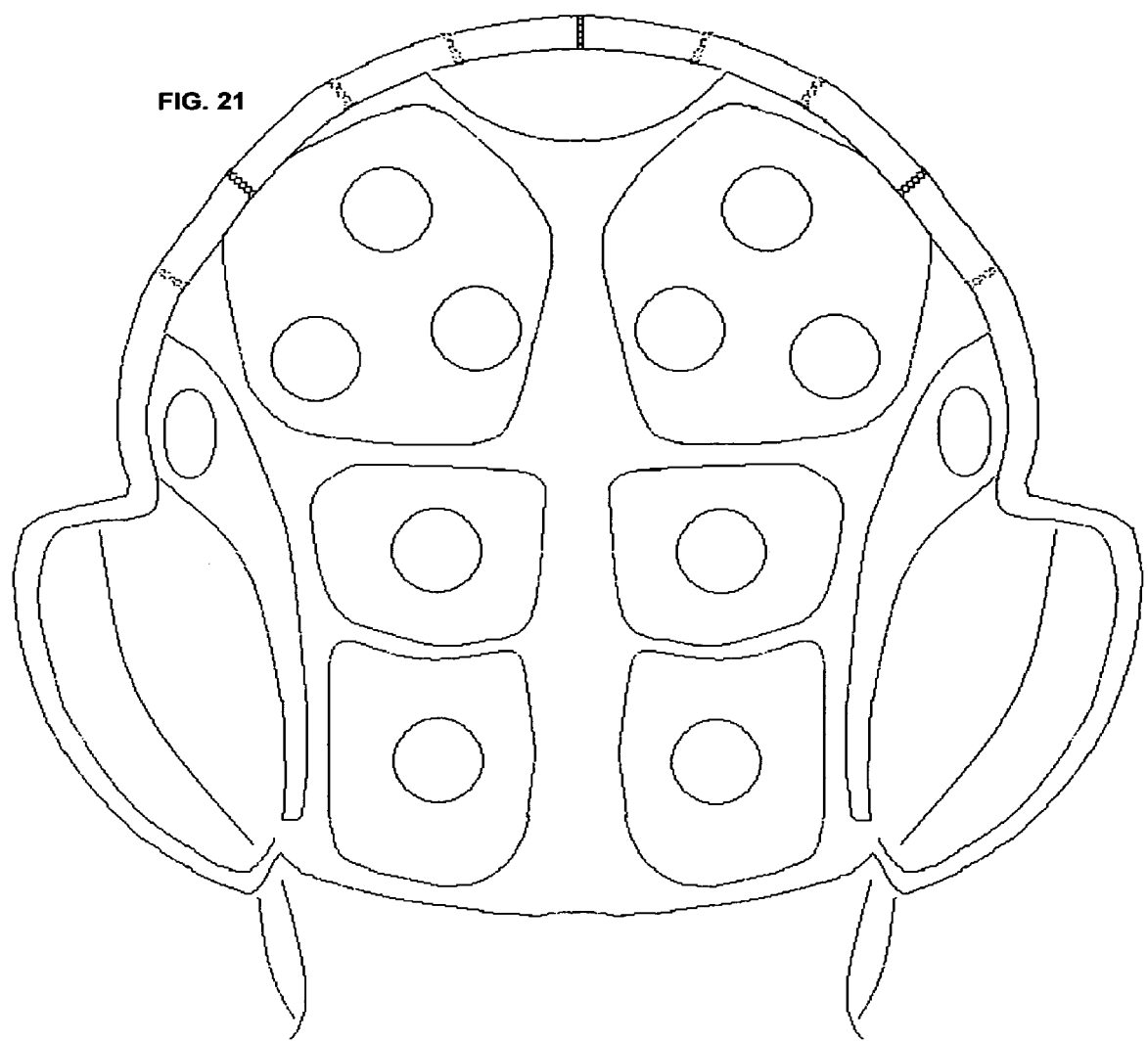
FIG. 21 shows FIG. 20 in solid lines.

FIG. 16, shows the front side view of the blind head cooling helmet, water pocket-magnet arrangement 58*a* will adapt into its parallel gel pocket-empty cavity arrangement 71*a*, 41*a*; water pocket-magnet arrangement 59*a* will adapt into its parallel gel pocket-empty cavity arrangement 72*a*, 41*a*; water pocket-magnet arrangement 60*a* will adapt into its parallel gel pocket-empty cavity arrangement 73*a*, 42*a*; water pocket-magnet arrangement 61*a* will adapt into its parallel gel pocket-empty cavity arrangement 74*a*, 43*a*; water pocket-magnet arrangement 58*b* will adapt into its parallel gel pocket-empty cavity arrangement 71*b*, 41*b*; water pocket-magnet arrangement 59*b* will adapt into its parallel gel pocket-empty cavity arrangement 72*b*, 41*b*; water pocket-magnet arrangement 60*b* will adapt into its parallel gel pocket-empty cavity arrangement 73*b*, 42*b*; water pocket-magnet arrangement 61*b* will adapt into its parallel gel pocket-empty cavity arrangement 74*b*, 43*b*; water pocket-magnet arrangement 55*a* will adapt into its parallel gel pocket-empty cavity arrangement 68*a*, 44*a*; water pocket-magnet arrangement 55*b* will adapt into its parallel gel pocket-empty cavity arrangement 68*b*, 44*b* water pocket-magnet arrangement 57*a* will adapt into its parallel gel pocket-empty cavity arrangement 70*a*, 45*a*; and finally the water pocket-magnet arrangement 57*b* will adapt into its parallel gel pocket-empty cavity arrangement 70*b*, 45*b*.

Figure 22:
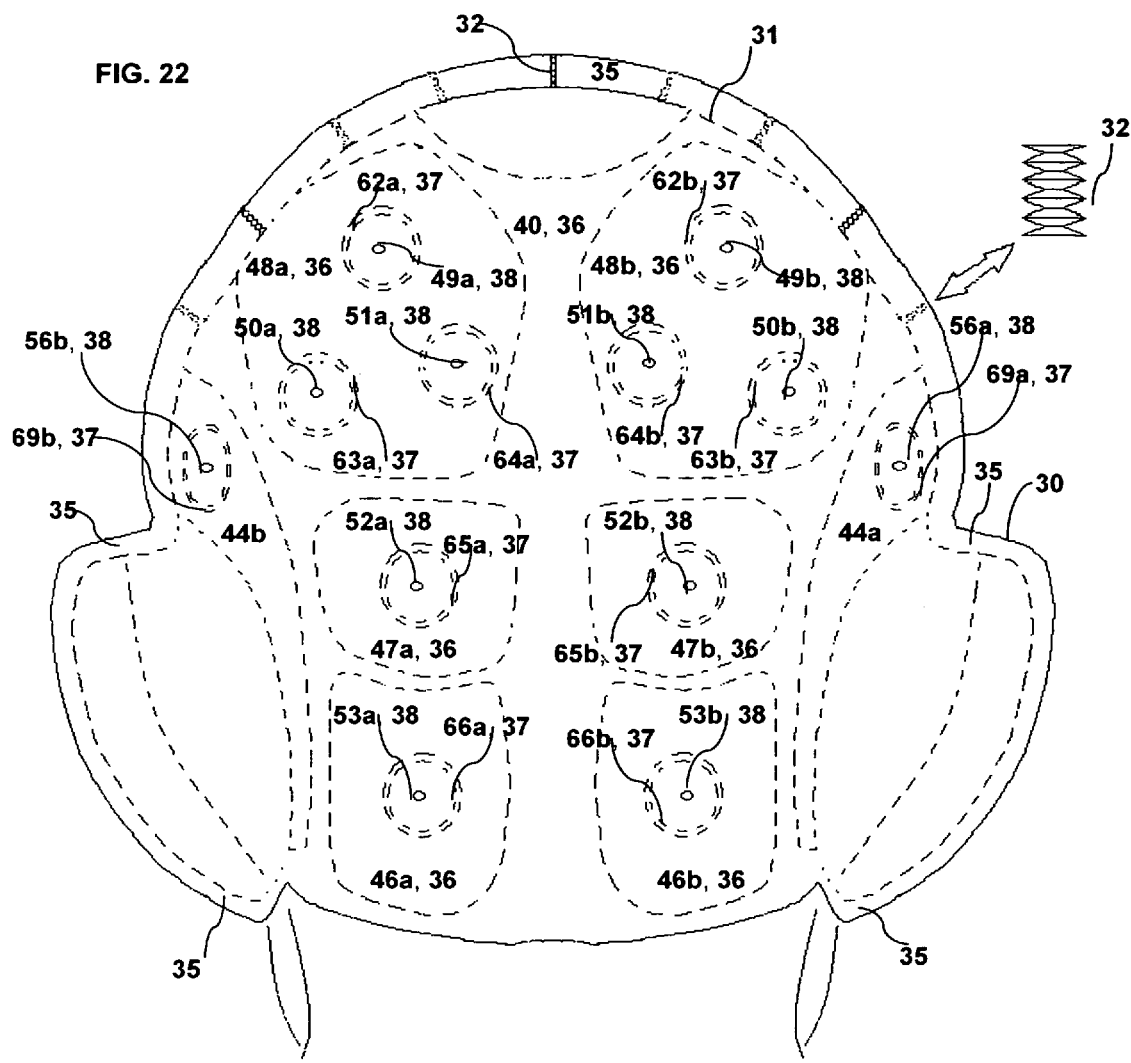
FIG. 22 shows the back side view of the blind head cooling helmet, with the internal layer 31 in dashed lines, as seen in FIG. 9 and FIG. 16, with the empty cavities 37 of its respective gel pockets 36 being adapted to the respective parallel water pockets 38 and magnets 26 not seen in this drawing.
Figure 23:
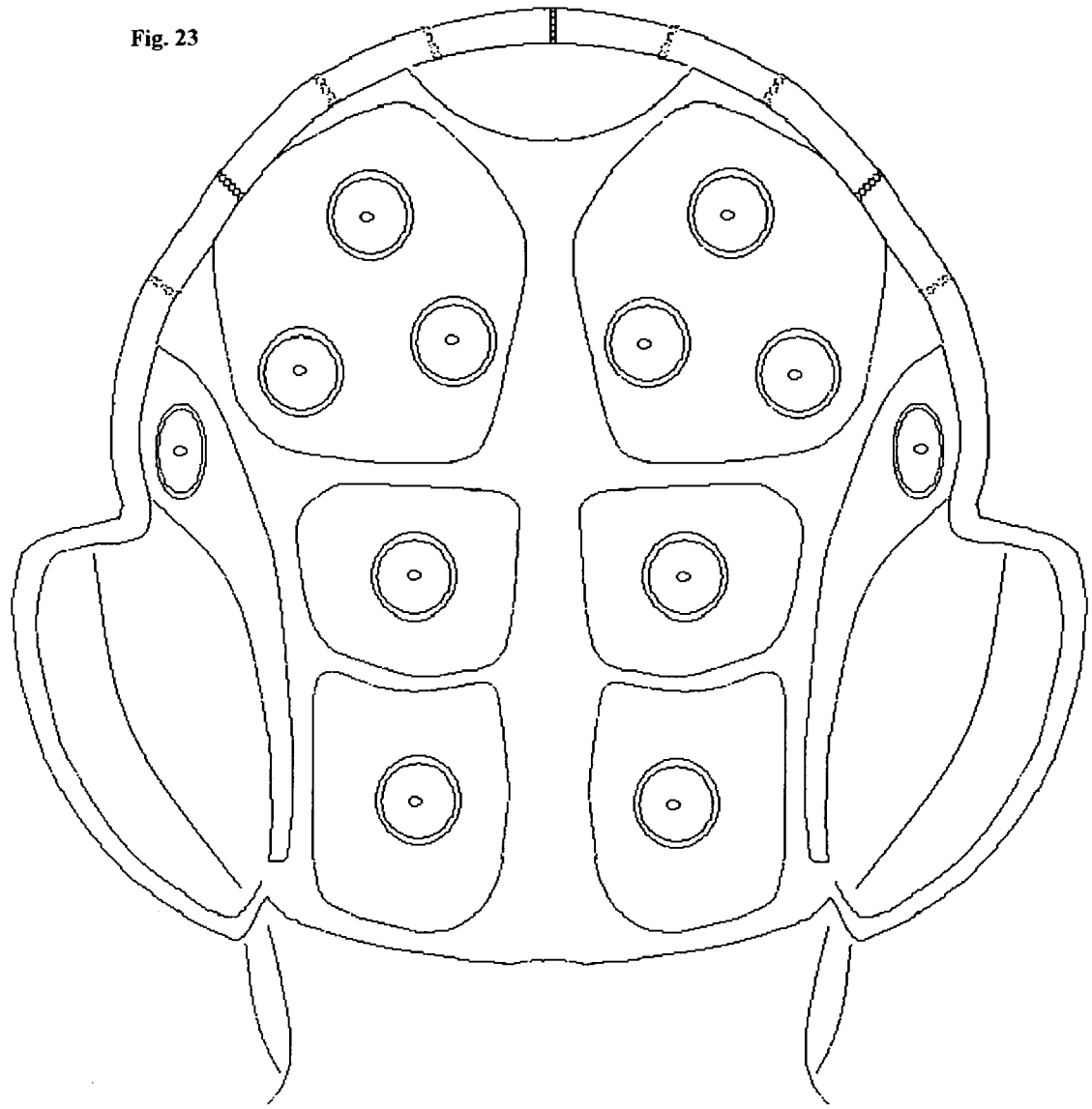
FIG. 23 shows FIG. 22 in solid lines.
Figure 24:
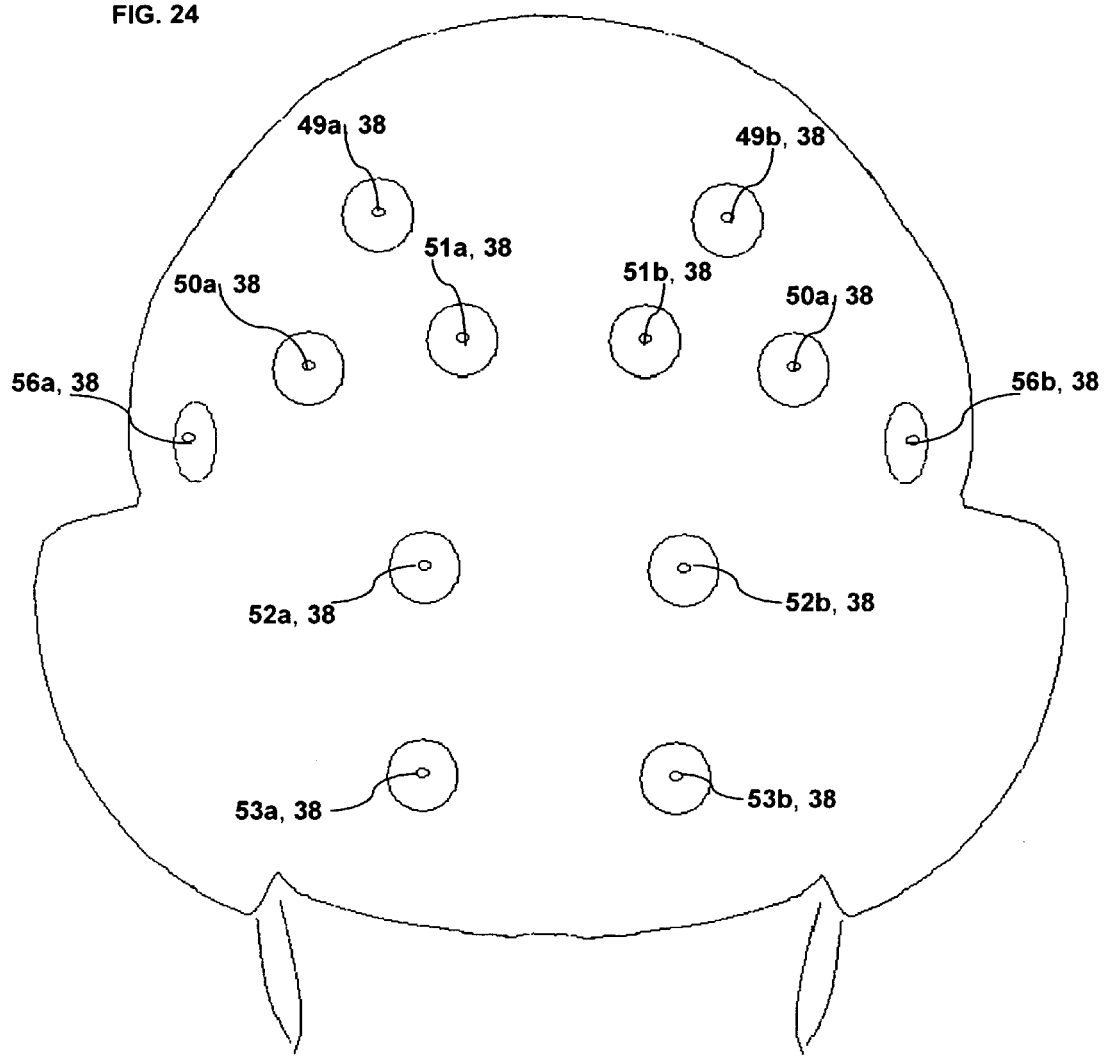
FIG. 24 shows a back view side of the blind head cooling helmet with its external surface 30 described in FIG. 11 and FIG. 18, with the external dry surfaces of the water pockets 38 and the respective tops or peaks 39 (dry roof 26a of the magnet 26).
Figure 25:
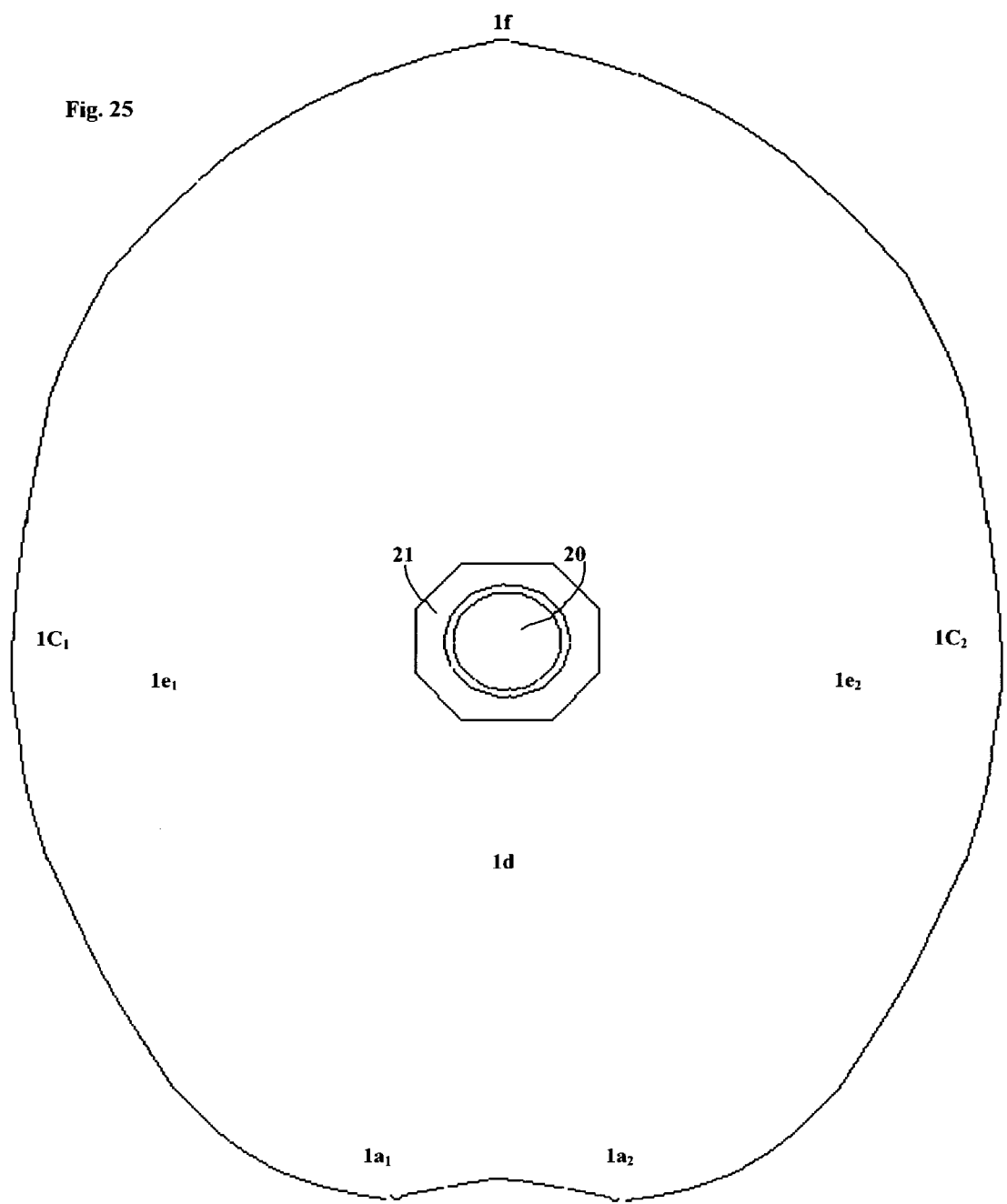
FIG. 25 shows the top side view of the blind head cooling helmet described in FIG. 5, FIG. 12 and FIG. 19 with the fore back 1f and covered forehead 1g, left side $1e_2$, right side $1e_1$, left eye $1a_2$, right eye $1a_1$, left ear $1c_2$ and right ear $1c_1$.
Figure 26:
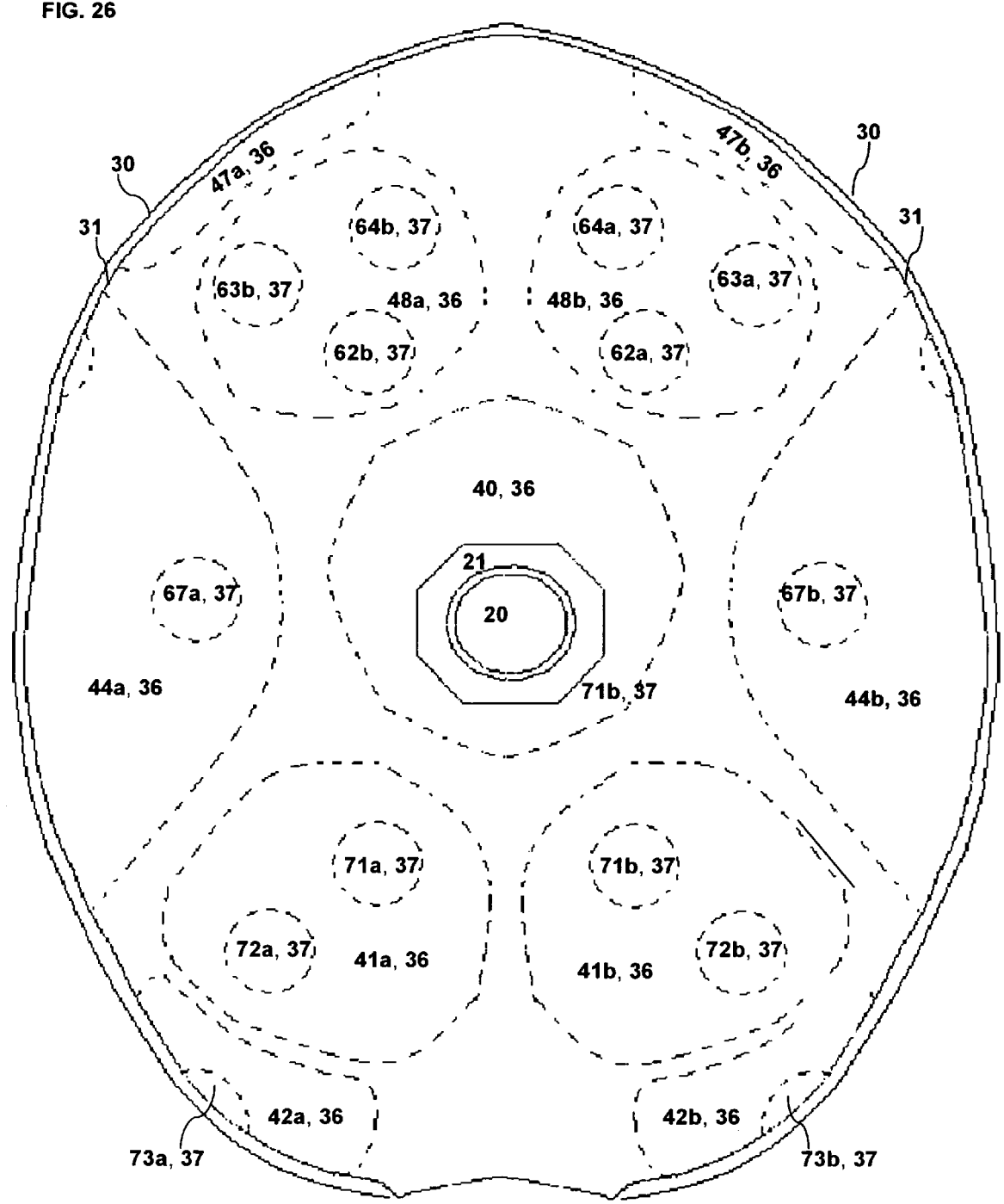
FIG. 26 shows a top side view of the blind head cooling helmet, in dashed lines, with the internal layer as seen in FIG. 7, FIG. 14 and FIG. 20, with the gel pockets 36 and its respective empty cavities 37.
Figure 27:
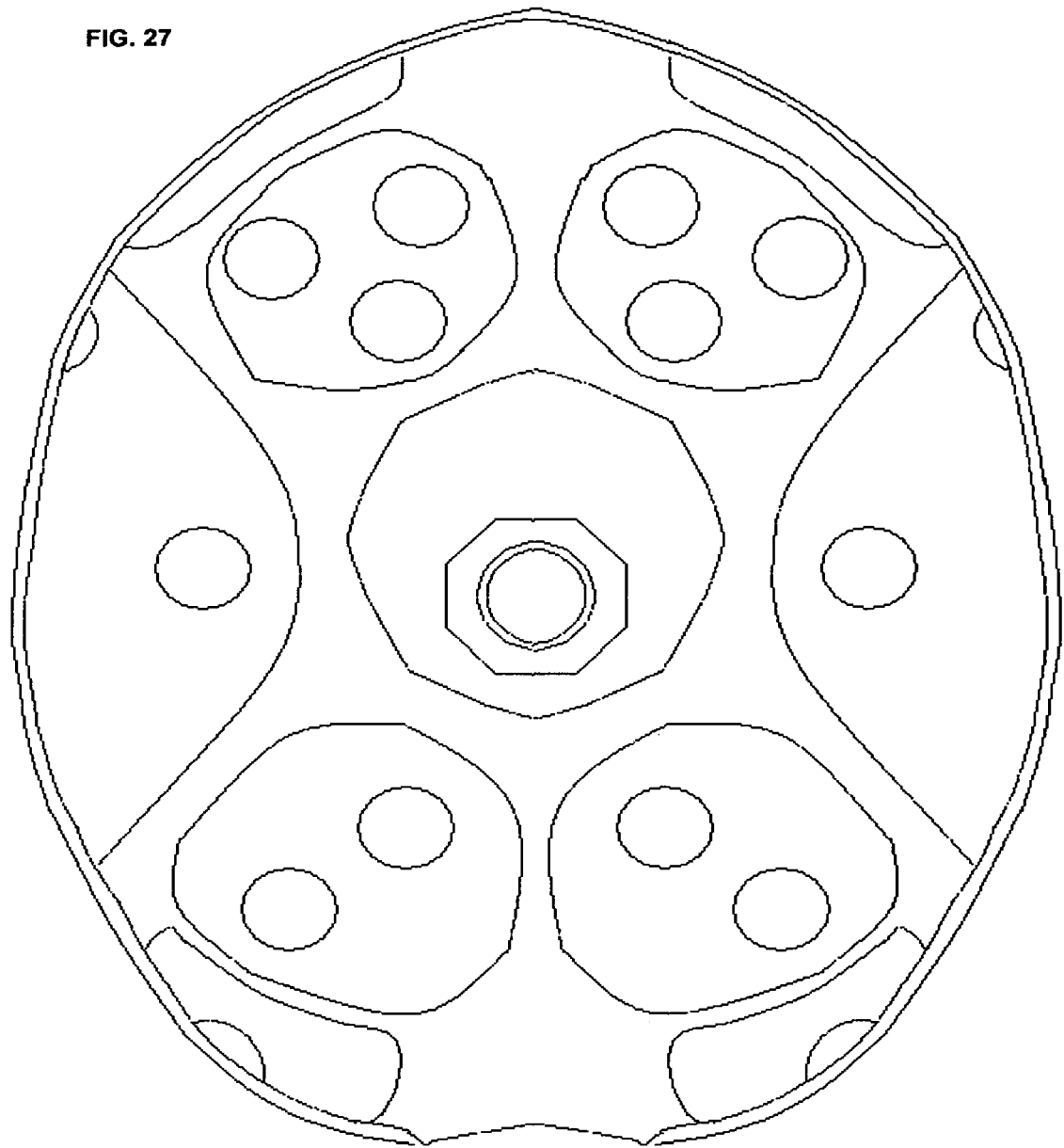
FIG. 27 shows FIG. 26 in solid lines.

FIG. 22, shows the back side view of the blind head cooling helmet, water pocket-magnet arrangement 49*a* will adapt into its parallel gel pocket-empty cavity arrangement 62*a*, 48*a*; water pocket-magnet arrangement 50*a* will adapt into its parallel gel pocket-empty cavity arrangement 63*a*, 48*a*; water pocket-magnet arrangement 51*a* will adapt into its parallel gel pocket-empty cavity arrangement 64*a*, 48*a*; water pocket-magnet arrangement 52*a* will adapt into its parallel gel pocket-empty cavity arrangement 65*a*, 47*a*; water pocket-magnet arrangement 53*a* will adapt into its parallel gel pocket-empty cavity arrangement 66*a*, 46*a*; water pocket-magnet arrangement 49*b* will adapt into its parallel gel pocket-empty cavity arrangement 62*b*, 48*b*; water pocket-magnet arrangement 50*b* will adapt into its parallel gel pocket-empty cavity arrangement 63*b*, 48*b*; water pocket-magnet arrangement 51*b* will adapt into its parallel gel pocket-empty cavity arrangement 64*b*, 48*b*; water pocket-magnet arrangement 52*b* will adapt into its parallel gel pocket-empty cavity arrangement 65*b*, 47*b*; water pocket-magnet arrangement 53*b* will adapt into its parallel gel pocket-empty cavity arrangement 66*b*, 46*b*; water pocket-magnet arrangement 56*b* will adapt into its parallel gel pocket-empty cavity arrangement 69*b*, 44*b*; water pocket-magnet arrangement 56*a* will adapt into its parallel gel pocket-empty cavity arrangement 69*a*, 44*a*; the covered ears portion are not seen in this drawing.

Figure 9:
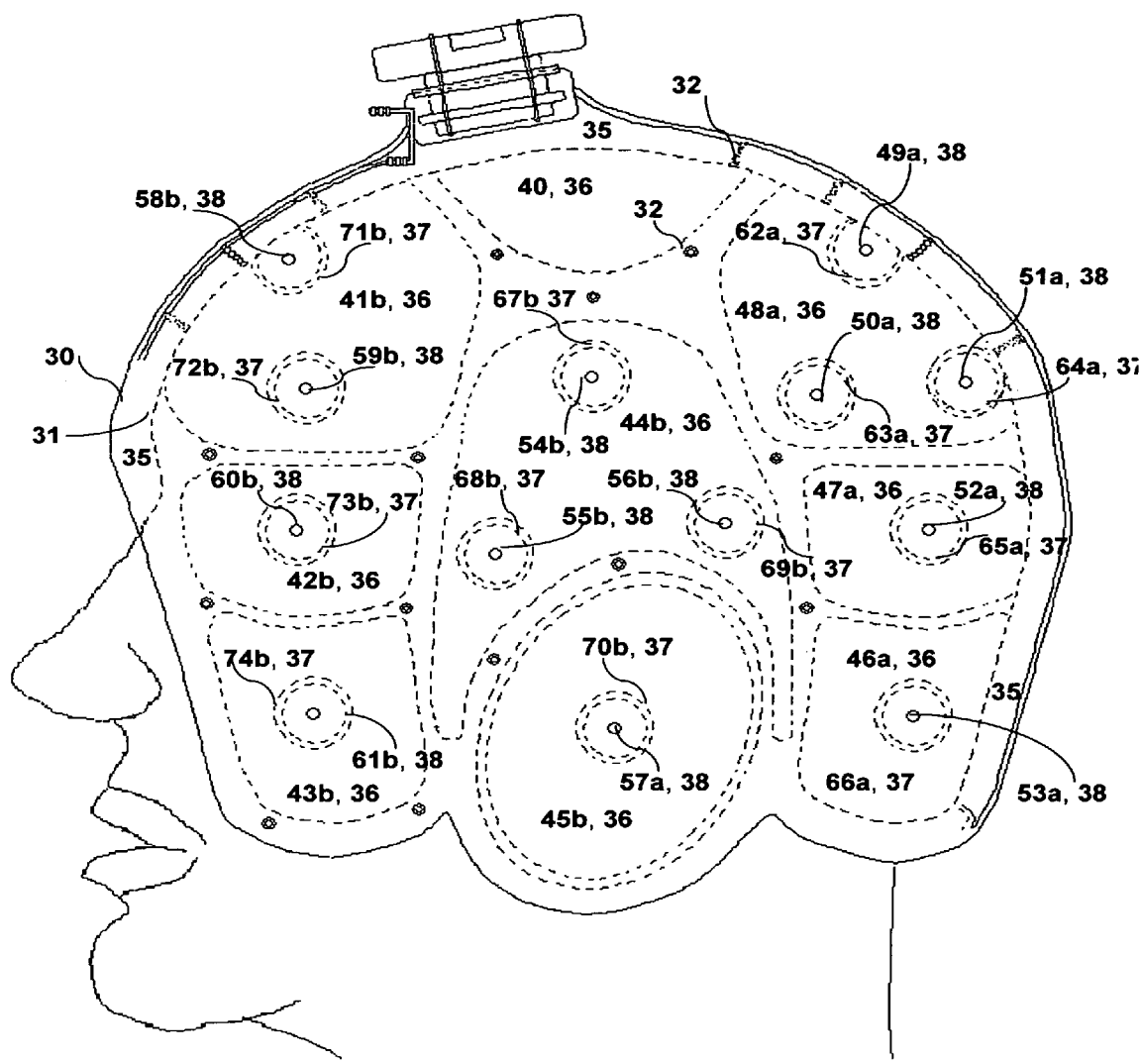
FIG. 9 shows a left side view of the blind head cooling helmet, with the internal layer 31 in dashed lines, with the empty cavities 37 of its respective gel pockets 36 being overlapped or adapted in with its respective parallel water pockets 38 and magnets 26, not seen in this drawing, where each one will be fully described in the Detailed Description of the Preferred Embodiment.
Figure 10:
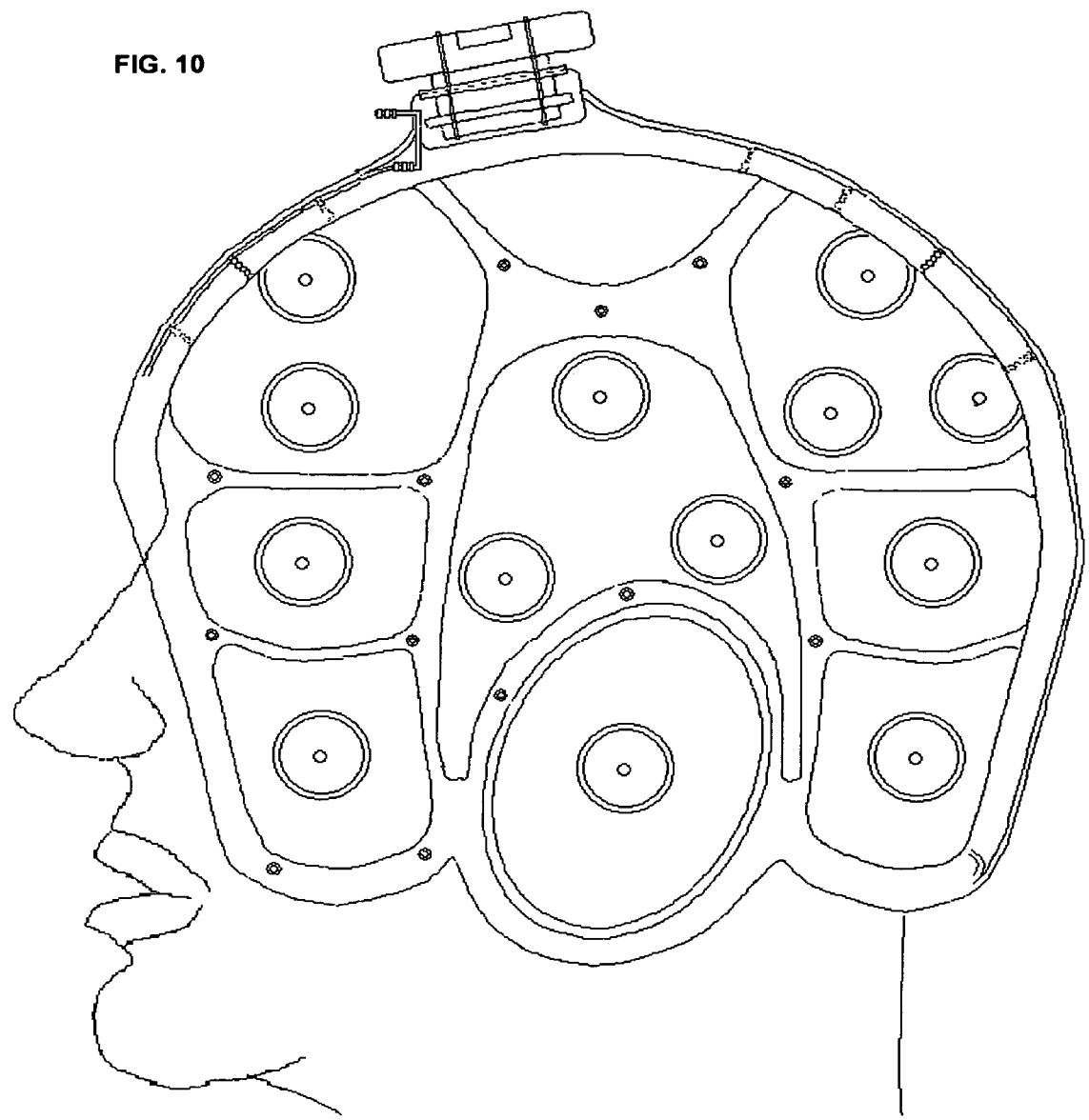
FIG. 10 shows FIG. 9 in solid lines.
Figure 11:
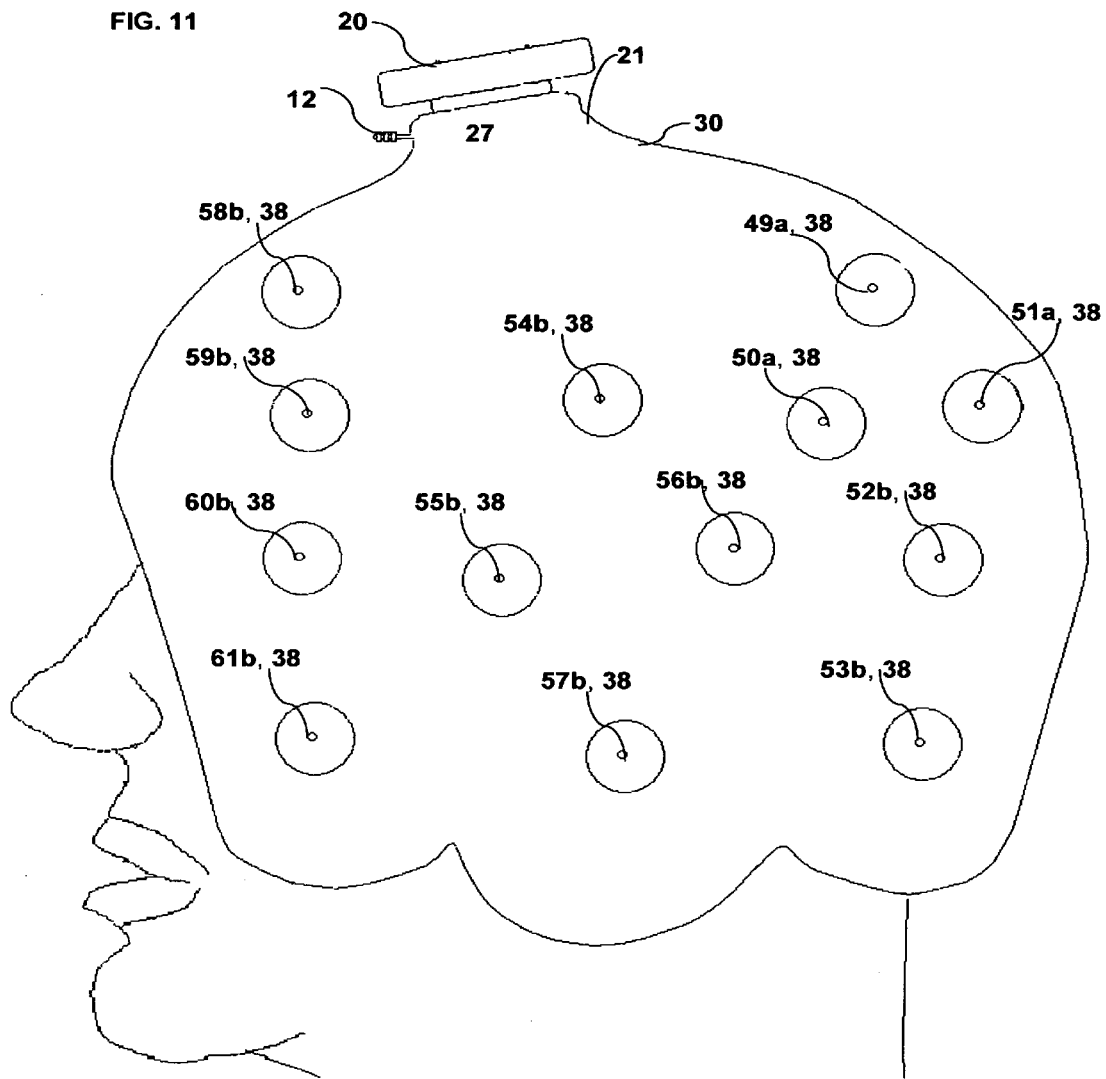
FIG. 11 shows a left side view of the blind head cooling helmet solely with the external surface 30 described in FIG. 5 and with the external dry surfaces of the water pockets 38 and its respective tops or peaks 39 (dry roof 26a of the magnet 26).
Figure 12:
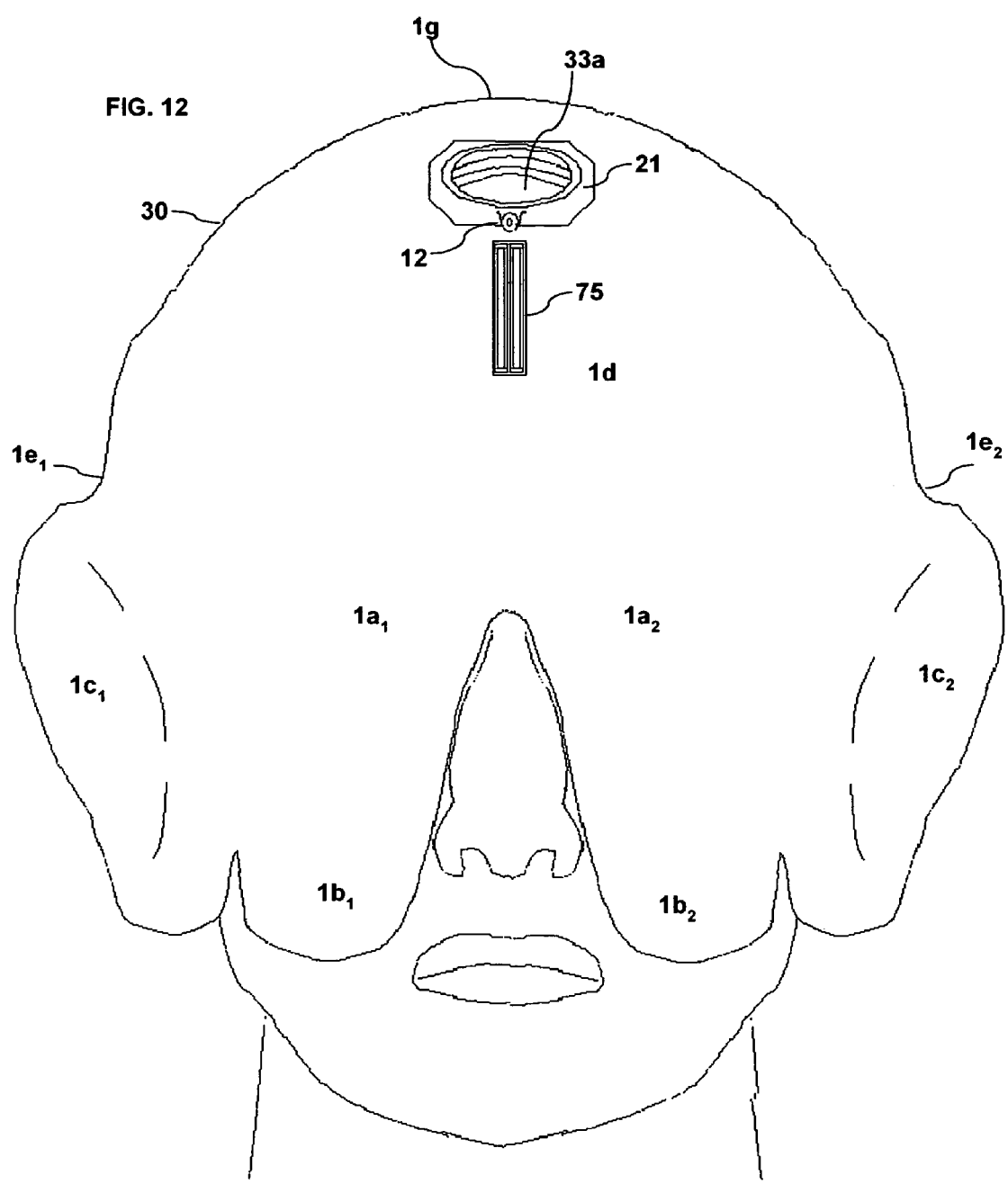
FIG. 12 shows the front side view of the blind head cooling helmet with the lid base 21, its air-inlet 12, the thermometer 75 on the forehead 1d and covered top 1g, right side $1e_1$, left side $1e_2$, right eye $1a_1$, left eye $1a_2$, right cheek $1b_1$ and left cheek $1b_2$ where are the surface is the external layer 30.
Figure 28:
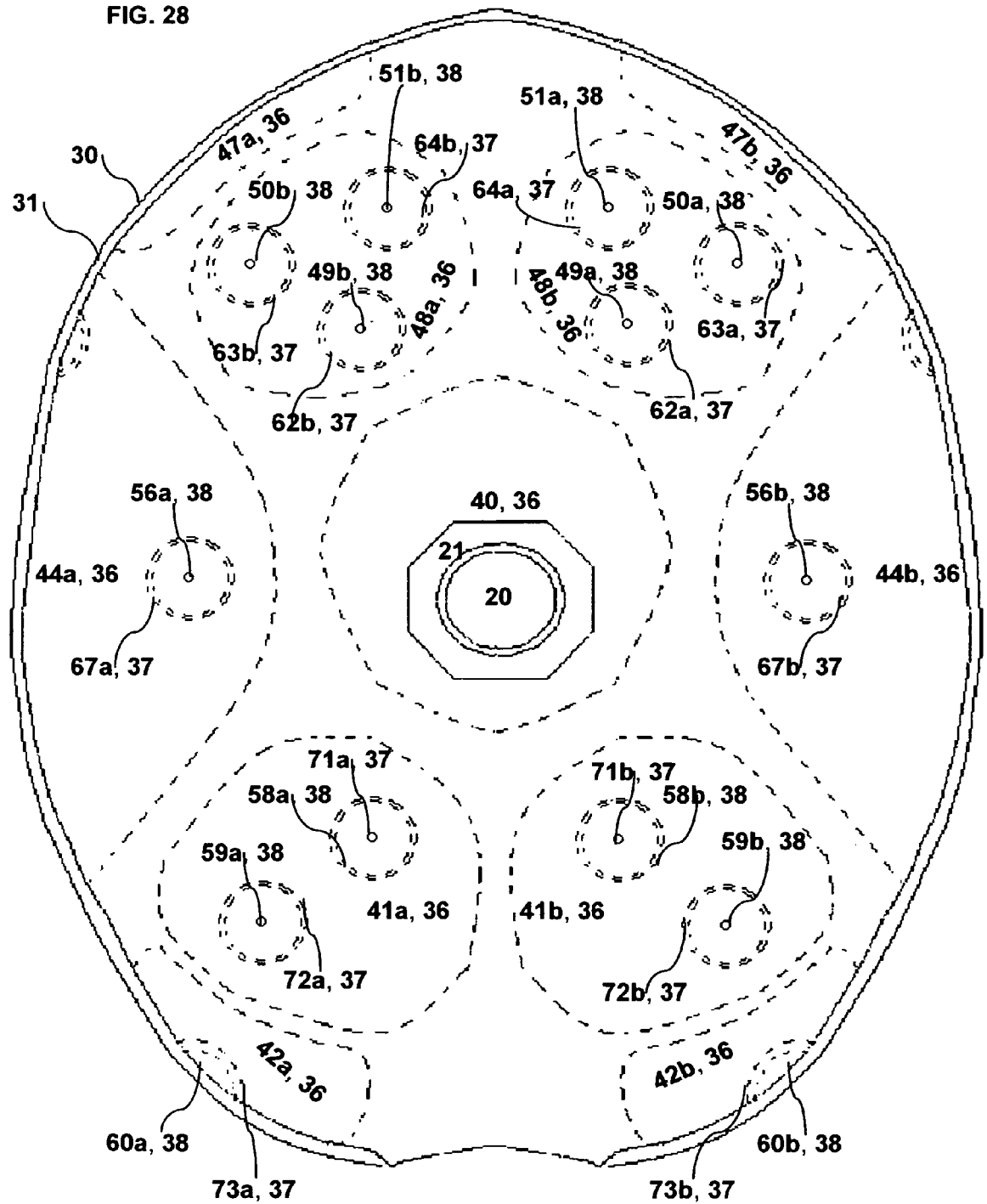
FIG. 28 shows a top view of the blind head cooling helmet, with the internal layer 31 in dashed lines, as seen in FIG. 9 and FIG. 16 and FIG. 22, with the empty cavities 37 of its respective gel pockets 36 being overlapped or adapted in with its respective parallel water pockets 38 and magnets 26, not seen in this drawing.
Figure 29:
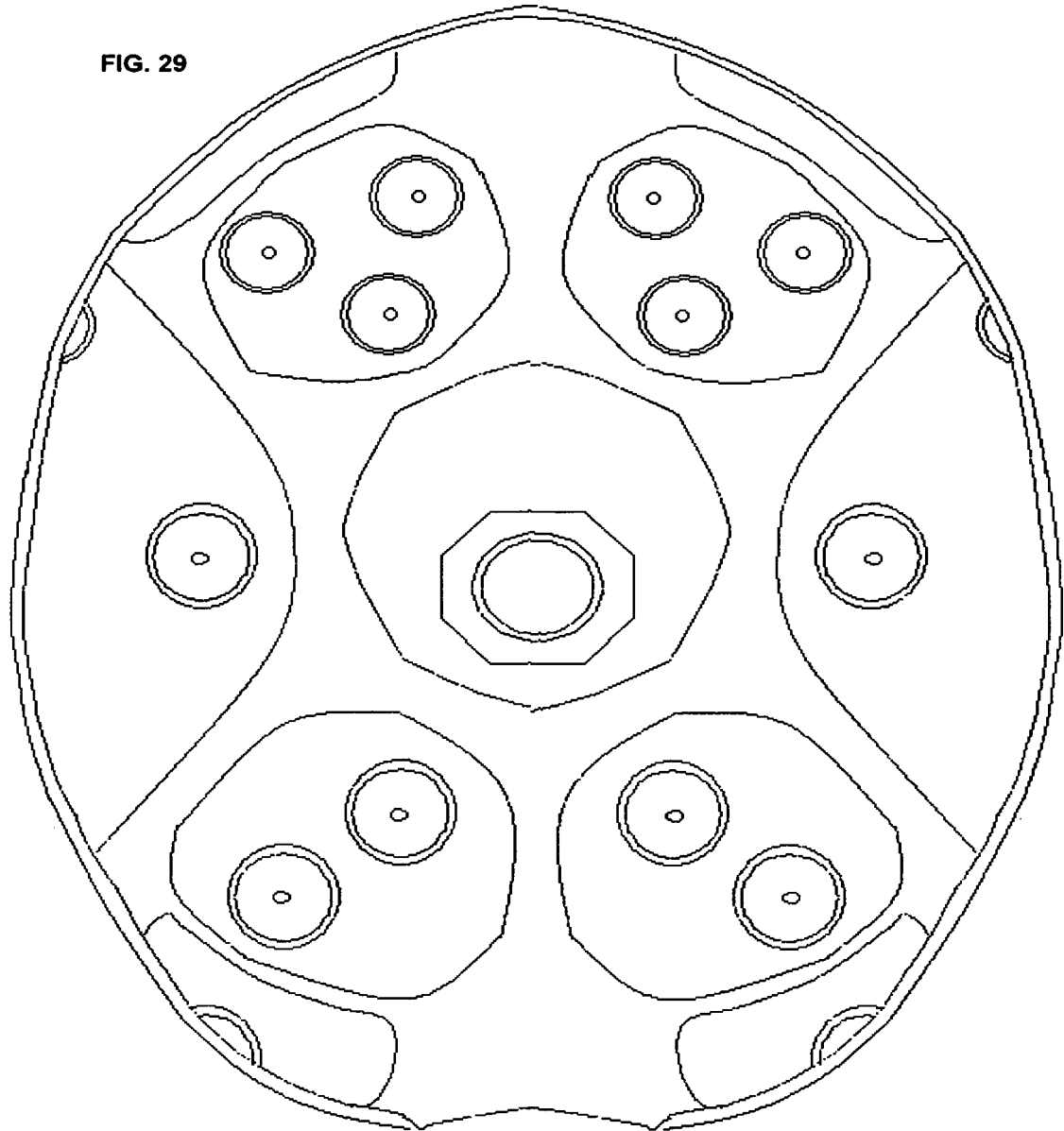
FIG. 29 shows FIG. 28 in solid lines.
Figure 30:
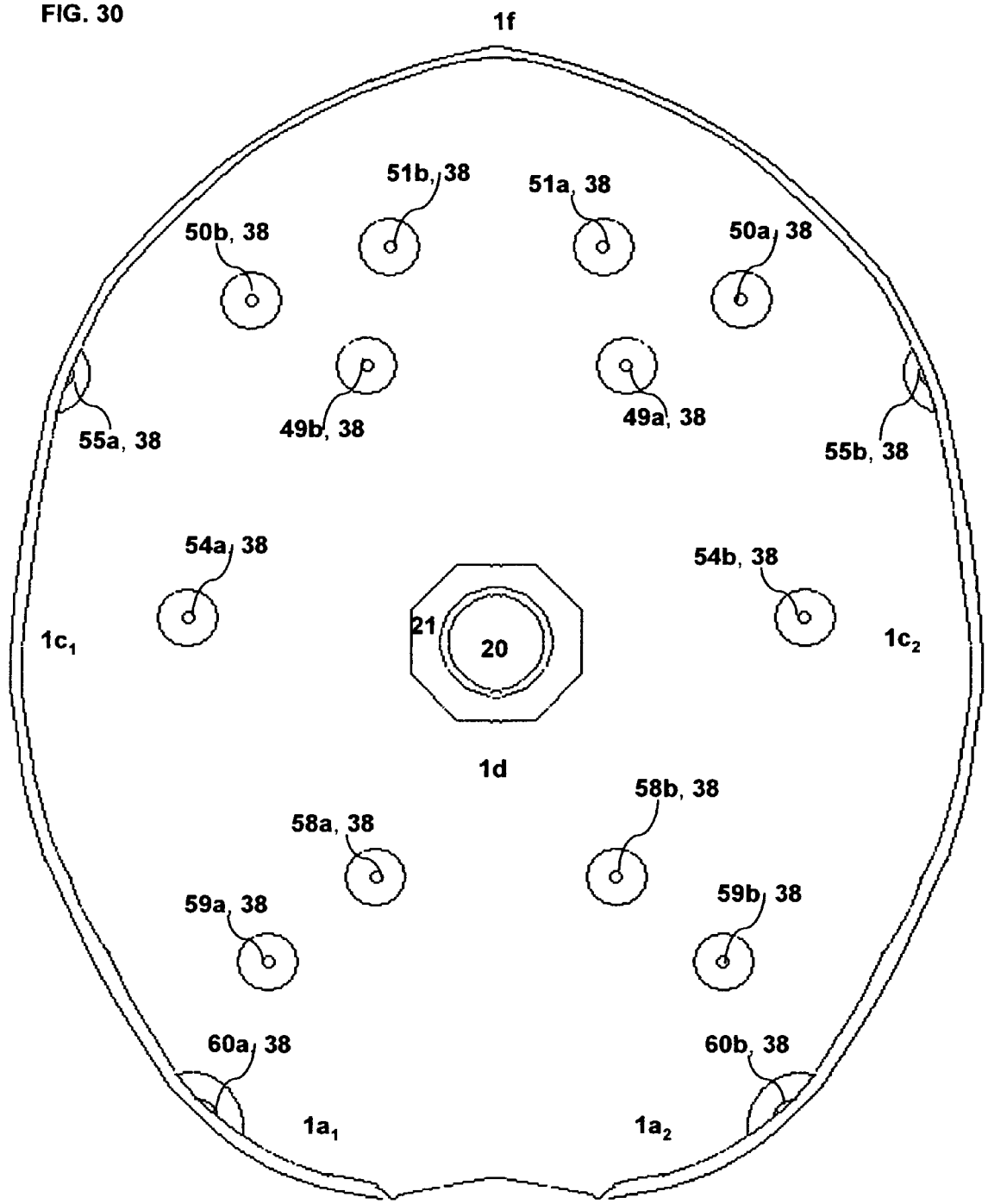
FIG. 30 shows a top view of the blind head cooling helmet with its external surface described in FIG. 11, FIG. 18 and FIG. 24, with the external dry surfaces of the water pockets 38 and its respective tops or peaks 39 (dry roof 26a of the magnet 26).

FIG. 28, shows the top side view of the blind head cooling helmet, is the same detailed explanation in FIG. 9, FIG. 16 and FIG. 22.

FIG. 11, FIG. 18, FIG. 24 and FIG. 30 shows the external layer 30, 30*a* of the blind head cooling helmet with the water pocket-magnet arrangement 38, 26 located in specific and determined areas. The external layer 30 comprises is a solid layer, this will be the real view ornamentally seen of the blind head cooling helmet but if the external layer 30 is manufactured of transparency basis all the internal layer 31 and its features will be also seen through.

It is understood that the preceding descriptions, explanations, and illustrations are given merely by way of illustration and not in limitation of the invention and that various modifications or embodiments may be made without departing from the spirit and scope of the invention as claimed.

What is claimed is:

1. An apparatus for reducing body temperature and alleviating headaches comprising:
   a contour mask that substantially covers the periphery of a human head; and
   a plurality of compartments distributed throughout said contour mask comprising:
      a first subset of said plurality of compartments having a first cooling-agent and at least one empty cavity;
      a second subset of said plurality of compartments having a second cooling agent;
      a third subset of said plurality of compartments having air, wherein said air is circulated throughout at least one hollow section of said contour mask; and
      a fourth subset of said plurality of compartments having at least one magnet and comprising a plurality of dome-like structures distributed throughout the outermost portion of said contour mask, wherein at least one of said at least one magnet is positioned on the uppermost portion of at least one of said dome-like structures.

2. The apparatus of claim 1, comprising: a plurality of flexible-elastic pins distributed at the uppermost portion of said contour mask, wherein at least one of said plurality of flexible-elastic pins provides the contour mask with at least one of: structural support and shock absorbing functions.

3. The apparatus of claim 1, wherein said air contacts said second cooling-agent, and wherein circulation of said air promotes free-flowing of said second cooling agent, thereby providing a user with a cooling effect and pain relief therapy.

4. The apparatus of claim 3, wherein at least one of said first cooling-agent and said second cooling-agent further comprises at least one of: a colloid, water, and a fluid agent.

5. The apparatus of claim 4, wherein a removable element allows introducing said second cooling-agent into said at least one hollow section of the contour mask.

6. The apparatus of claim 5, wherein said removable element comprises at least one crevice for attaching at least one of: a watch and a digital thermometer.

7. The apparatus of claim 5, wherein said removable element comprises at least one of: an air inlet and an air outlet.

8. The apparatus of claim 7, wherein said at least one hollow section of the contour mask comprises an intermediate skeleton, wherein said intermediate skeleton has perforated air-duct means and whereby said air is introduced into said intermediate skeleton via said at least one air inlet.

9. The apparatus of claim 8, wherein said air exits said intermediate skeleton via said perforated air-duct means in the form of air bubbles.

10. The apparatus of claim 9, wherein said first subset of said compartments, said second subset of said compartments and said intermediate skeleton are distributed on a substantially parallel position to each other; and wherein said first subset of said compartments, said second subset of said compartments and said intermediate skeleton are enclosed between polymer-material layers.

11. The apparatus of claim 10, wherein said air bubbles are released into said second subset of said compartments; and wherein said air bubbles interact with said second-cooling agent to promote flow of said second-cooling agent throughout said contour mask.

12. The apparatus of claim 1, wherein said first subset of compartments having a first cooling-agent are attached to said at least one hollow section of the contour mask; said first cooling-agent is substantially in direct contact with said human head; and whereby said direct contact provides a user with a cooling effect and pain relief therapy.

13. The apparatus of claim 1, wherein said contour mask substantially covers at least one of: a forehead section, a back head section, a left temple side, a right temple side, a left cheek side, a right cheek side, a left ear side, a right ear side, a left eye and a right eye of said user.

14. The apparatus of claim 1, wherein at least one dome-like structure of said plurality of dome-like structures is positioned directly above said at least one empty cavity.

15. The apparatus of claim 1, wherein said plurality of dome-like structures and said at least one empty cavity are filled with said second-cooling agent; wherein at least one of said plurality of dome-like structures is depressed into said at least one empty cavity; and whereby the action of depressing at least one of said plurality of dome-like structures into said at least one empty cavity allows at least one of said at least one magnet to come substantially in direct contact with said human head of said user.

* * * * *